United States Patent [19]

Wilding et al.

[11] Patent Number: 5,637,469

[45] Date of Patent: *Jun. 10, 1997

[54] METHODS AND APPARATUS FOR THE DETECTION OF AN ANALYTE UTILIZING MESOSCALE FLOW SYSTEMS

[75] Inventors: Peter Wilding, Paoli; Larry J. Kricka, Berwyn; Jay N. Zemel, Jenkintown, all of Pa.

[73] Assignee: Trustees of the University of Pennsylvania, Philadelphia, Pa.

[*] Notice: The term of this patent shall not extend beyond the expiration date of Pat. No. 5,304,487.

[21] Appl. No.: 347,498

[22] Filed: Nov. 30, 1994

Related U.S. Application Data

[63] Continuation of Ser. No. 877,702, May 1, 1992, abandoned.

[51] Int. Cl.⁶ .................. G01N 33/43; G01N 33/551; G01N 33/558; G01N 33/569
[52] U.S. Cl. .................. 435/7.21; 422/55; 422/56; 422/57; 422/58; 435/7.2; 435/287.1; 435/287.2; 435/287.9; 435/288.4; 435/288.5; 435/288.7; 435/810; 435/970; 435/6; 436/164; 436/518; 436/514; 436/524; 436/527; 436/531; 436/533; 436/534; 436/805; 436/806; 436/807; 436/809
[58] Field of Search .................. 422/55–58; 435/7.2, 435/7.21, 259, 291, 287.1, 287.2, 287.9, 288.4, 288.5, 288.7, 810, 970, 6; 436/164, 518, 524, 527, 531, 533, 534, 805, 806, 807, 809, 514

[56] References Cited

U.S. PATENT DOCUMENTS

| | | | |
|---|---|---|---|
| 3,799,742 | 3/1974 | Coleman | 422/61 |
| 4,233,029 | 11/1980 | Columbus | 422/55 |
| 4,302,313 | 11/1981 | Columbus | 422/68 |
| 4,618,476 | 10/1986 | Columbus | 422/100 |
| 4,790,640 | 12/1988 | Nason . | |
| 4,886,761 | 12/1989 | Gustafson et al. | 436/524 |
| 4,906,439 | 3/1990 | Grenner | 422/56 |
| 4,908,112 | 3/1990 | Pace | 356/318 |
| 4,911,782 | 3/1990 | Brown | 156/633 |
| 4,963,498 | 10/1990 | Hillman | 436/69 |
| 4,999,283 | 3/1991 | Zavos et al. . | |
| 5,135,720 | 8/1992 | Uchida | 422/107 |
| 5,147,606 | 9/1992 | Charlton | 422/56 |
| 5,304,487 | 4/1994 | Wilding et al. | 422/55 |

FOREIGN PATENT DOCUMENTS

| | | |
|---|---|---|
| 0320308 | 6/1989 | European Pat. Off. . |
| 0430248 | 6/1991 | European Pat. Off. . |
| 0439182 | 7/1991 | European Pat. Off. . |
| 0483117 | 4/1992 | European Pat. Off. . |
| 3915920 | 11/1990 | Germany . |

(List continued on next page.)

OTHER PUBLICATIONS

Pfahler, et al., "Liquid Transport in Micron and Submicron Channels," *Sensors and Actuators A*, 21–23:431–434 (1990).

(List continued on next page.)

*Primary Examiner*—Christopher L. Chin
*Attorney, Agent, or Firm*—Dann, Dorfman, Herrell and Skillman

[57] ABSTRACT

Disclosed are devices for detecting the presence of a preselected analyte in a fluid sample. The devices comprise a substrate microfabricated to define a sample inlet port, and a mesoscale flow system that includes a sample flow channel extending from the inlet port. The mesoscale flow system further includes an analyte detection region in fluid communication with the flow channel comprised of a binding moiety for specifically binding the analyte. The detection region is constructed with a mesoscale dimension sufficiently small to enhance binding of the binding moiety and the analyte. The binding moiety may be immobilized in the detection region. The mesoscale detection systems of the invention may be used in a wide range of applications, including the detection of cells or macromolecules, or for monitoring reactions or cell culture growth.

44 Claims, 13 Drawing Sheets

FOREIGN PATENT DOCUMENTS

| | | |
|---|---|---|
| 2191110 | 12/1987 | United Kingdom. |
| 2204398 | 9/1988 | United Kingdom. |
| 90/09596 | 8/1990 | WIPO. |
| WO91/13338 | 9/1991 | WIPO. |
| 91/16966 | 11/1991 | WIPO. |

OTHER PUBLICATIONS

Anderson, *Nature*, 355:379 (1992).

Angell, et al., *Scientific American*, 248:44–55 (1983).

Appenzeller, *Science*, 254:1300–1342 (1991).

Barany, *Proc. Natl. Acad. Sci.*, 88:189–192 (1991).

Brown, "Development of a Stopped–Flow Cytometer," NSF Grant No. ISI 87–60730.

Brunette, *Exper. Cell Res.*, 167: 203–217 (1986).

Brunette, *Exper. Cell. Res.*, 164: 11–26 (1986).

Columbus et al., *Clin. Chem.*, 33:1531–1537 (1987).

DeLuca et al., *Arch. Biochem. Biophys.*, 255:285–292 (1983).

Dessy, *Chemometrics and Intelligent Laboratory Systems*, 8:311 (1990) Abstract.

Esashi et al., "Integrated Flow Control Systems Fabricated on a Silicon Wafer," Proceedings, Electrochemical Society Conference, HI (18–23 Oct. 1987), Electrochemical Society, Pennington, NJ, pp. 31–38B, 1987.

Fromherz et al., *Biochemica et Biophysica Acta*, 1062:103–107 (1991).

Goin et al., *Clin. Chem.*, 32:1655–1659 (1986).

Haller in: *Solid Phase Biochemistry*, W.H. Scouten, Ed., John Wiley, New York, pp. 535–597 (1983).

Hanazato et al., *IEEE Transactions Electron. Devices*; ED33:47–51 (1986).

Hoopma, "Microchanneled Structures," Applied Technology Laboratory, 3M Center, St. Paul, MN55144–55144–1000.

Howe et al., *IEEE Transactions Electron Devices*, ED33:499–506. (1986).

Hung et al, *Med. & Biol. Engng.*, 9:237–245 (1971).

Jonsson, *Methods in Enzymology*, 137:381–389 (1988).

Kennedy et al., *Clin. Chem. Acta.*, 70:1–31 (1976).

Kenny et al., *Appl. Phys. Lett.*, 58:100–102 (1991).

Kikuchi et al., "Microchannels Made on Silicon Wafer for Measurement of Flow Properties of Blood Cells," *Biortheology*, 26:1055 (1989), Abstract.

Kittilsland et al., *Journal de Physique*, 49 (C4):641–644 (1988).

Kittilsland et al., *Sensors and Activators*, A21–A23:904–907 (1990).

Kricka et al., "Liquid Transport in Micron and Submicron Channels," *SPIE*, 1167:159–168 (1989).

Kricka et al., *Clin. Chem.*, 26:741–744 (1980).

LaCelle, *Blood Cells*, 12:179–189 (1986).

Mandenius et al., *Anal. Biochem.*, 137:106–114 (1984).

Mandenius et al., *Anal. Biochem.*, 170:68–72 (1988).

Mandenius et al., *Methods in Enzymology*, 137:388–394 (1988).

Manz et al., *Trends in Anal. Chem.*, 10:144–149 (1991).

Masuda et al., *Proc. IEEE/IAS Meeting*, pp. 1549–1553 (1987).

McCartney et al., *Cancer Res.*, 41:3046–3051 (1981).

Moghissi et al., *Am. J. Obst. Gynecol.*, 114:405–(1972).

Nakamura, *Immunochemical Assays and Biosensor Technology for the 1990's*, American Society of Microbiology, Washington, D.C., pp. 205–215 (1992).

Nakamura et al., *Anal. Chem.*, 63:268–272 (1991).

Parce et al., *Science*, 24:243–247 (1989).

Rosenberg et al., *Clin. Chem.*, 30:1462–1466 (1984).

Rosenberg et al., *Clin. Chem.*, 31:1444–1448 (1985).

Sankolli et al., *J. Imun. Methods*, 104:191–194 (1987).

Sato, et al., *Sensors and Actuators*, A21–A23:948–951 (1990).

Shoji, et al., *Sensors and Actuators*, 15:101–107 (1988).

Stange et al., *Biomaterials*, 9:3–6 (1988).

Van Lintel, *Sensors and Actuators*, 15:153–167 (1988).

Wallis et al., *J. Amer. Ceramic Soc.*, 53:563–567 (1970).

Washizu et al., *Proceedings IEEE/IAS Meeting*, pp. 1735–1740 (1988).

Weissman et al., *Am Inst. Chem. Eng. J.* 17:25–30 (1971).

Zemel et al. in: *Fundamentals and Applications of Chemical Sensors*, D. Schuetzle and R. Hammerle, Eds., Washington, D.C., 1986, pp. 2–38.

Biotrack, Ciba Corning, May, 1989.

Wilding, *Advanced Hospital Technology Laboratory*, Oct., 1990 pp. 38–42.

Roche, On–Trak™, Sep., 1988.

Angell et al., *Scientific American*, 248:44–55 (1983).

Appenzeller, *Science*, 254:1300–1342 (1991).

Brown, "Development of a Stopped–Flow Cytometer," NSF Grant No. ISI 87–60730, Abstract.

Brunette, *Exper. Cell Res.*, 167:203–217 (1986).

Brunette, *Exper. Cell. Res.*, 164:11–26 (1986).

Kinosita et al., "Dual–View Microscopy With A Single Camera: Real–Time Imaging Of Molecular Orientations And Calcium," *J. Cell Biol*, 115:67–73 (1991) (Abstract).

METHODS AND APPARATUS FOR THE DETECTION OF AN ANALYTE UTILIZING MESOSCALE FLOW SYSTEMS

This is a continuation of application Ser. No. 07/877,702, filed May 1, 1992.

REFERENCE TO RELATED APPLICATIONS

This application is being filed contemporaneously with the following related co-pending applications: U.S. application Ser. No. 07/887,701, now abandoned; U.S. application Ser. No. 07/887,536, now U.S. Pat. No. 5,304,487, issued Apr. 19, 1994; U.S. application Ser. No. 07/887,662, now abandoned; and U.S. application Ser. No. 07/887,661, now U.S. Pat. No. 5,296,375, issued Mar. 22, 1994.

Continuation applications have been filed based on the above-noted abandoned applications, all of which are currently pending.

BACKGROUND OF THE INVENTION

This invention relates generally to methods and apparatus for conducting analyses. More particularly, the invention relates to the design and construction of small, typically single-use, modules capable of receiving and rapidly conducting a predetermined assay protocol on a fluid sample.

In recent decades the art has developed a very large number of protocols, test kits, and cartridges for conducting analyses on biological samples for various diagnostic and monitoring purposes. Immunoassays, agglutination assays, and analyses based on polymerase chain reaction, various ligand-receptor interactions, and differential migration of species in a complex sample all have been used to determine the presence or concentration of various biological compounds or contaminants, or the presence of particular cell types.

Recently, small, disposable devices have been developed for handling biological samples and for conducting certain clinical tests. Shoji et al. reported the use of a miniature blood gas analyzer fabricated on a silicon wafer. Shoji et al., *Sensors and Actuators*, 15:101–107 (1988). Sato et al. reported a cell fusion technique using micromechanical silicon devices. Sato et al., *Sensors and Actuators*, A21–A23:948–953 (1990). Ciba Corning Diagnostics Corp. (USA) has manufactured a microprocessor-controlled laser photometer for detecting blood clotting.

Micromachining technology originated in the microelectronics industry. Angell et al., *Scientific American*, 248:44–55 (1983). Micromachining technology has enabled the manufacture of microengineered devices having structural elements with minimal dimensions ranging from tens of microns (the dimensions of biological cells) to nanometers (the dimensions of some biological macromolecules). This scale is referred to herein as "mesoscale". Most experiments involving mesoscale structures have involved studies of micromechanics, i.e., mechanical motion and flow properties. The potential capability of mesoscale structures has not been exploited fully in the life sciences.

Brunette (*Exper. Cell Res.*, 167:203–217 (1986) and 164:11–26 (1986)) studied the behavior of fibroblasts and epithelial cells in grooves in silicon, titanium-coated polymers and the like. McCartney et al. (*Cancer Res.*, 41:3046–3051 (1981)) examined the behavior of tumor cells in grooved plastic substrates. LaCelle (*Blood Cells*, 12:179–189 (1986)) studied leukocyte and erythrocyte flow in microcapillaries to gain insight into microcirculation.

Hung and Weissman reported a study of fluid dynamics in micromachined channels, but did not produce data associated with an analytic device. Hung et al., *Med. and Biol. Engineering*, 9:237–245 (1971); and Weissman et al., *Am. Inst. Chem. Eng. J.*, 17:25–30 (1971). Columbus et al. utilized a sandwich composed of two orthogonally orientated v-grooved embossed sheets in the control of capillary flow of biological fluids to discrete ion-selective electrodes in an experimental multi-channel test device. Columbus et al., *Clin. Chem.*, 33:1531–1537 (1987). Masuda et al. and Washizu et al. have reported the use of a fluid flow chamber for the manipulation of cells (e.g. cell fusion). Masuda et al., *Proceedings IEEE/IAS Meeting*, pp. 1549–1553 (1987); and Washizu et al., *Proceedings IEEE/IAS Meeting* pp. 1735–1740 (1988). The art has not fully explored the potential of using mesoscale devices for the analyses of biological fluids and detection of microorganisms.

The current analytical techniques utilized for the detection of microorganisms are rarely automated, usually require incubation in a suitable medium to increase the number of organisms, and invariably employ visual and/or chemical methods to identify the strain or sub-species. The inherent delay in such methods frequently necessitates medical intervention prior to definitive identification of the nature of an infection. In industrial, public health or clinical environments, such delays may have serious consequences. There is a need for convenient systems for the rapid detection of microorganisms.

An object of the invention is to provide analytical systems with optimal reaction environments that can analyze microvolumes of sample, detect substances present in very low concentrations, and produce analytical results rapidly. Another object is to provide easily mass produced, disposable, small (e.g., less than 1 cc in volume) devices having mesoscale functional elements capable of rapid, automated analyses of preselected molecular or cellular analytes, in a range of biological and other applications. It is a further object of the invention to provide a family of such devices that individually can be used to implement a range of rapid clinical tests, e.g., tests for bacterial contamination, virus infection, sperm motility, blood parameters, contaminants in food, water, or body fluids, and the like.

SUMMARY OF THE INVENTION

The invention provides methods and devices for the detection of a preselected analyte in a fluid sample. The device comprises a solid substrate, typically on the order of a few millimeters thick and approximately 0.2 to 2.0 centimeters square, microfabricated to define a sample inlet port and a mesoscale flow system. The term "mesoscale" is used herein to define chambers and flow passages having cross-sectional dimensions on the order of 0.1 µm to 500 µm. The mesoscale flow channels and fluid handling regions have a preferred depth on the order of 0.1 µm to 100 µm, typically 2–50 µm. The channels have preferred widths on the order of 2.0 µm to 500 µm, more preferably 3–100 µm. For many applications, channels of 5–50 µm widths will be useful. Chambers in the substrates often will have larger dimensions, e.g., a few millimeters.

The mesoscale flow system of the device includes a sample flow channel, extending from the inlet port, and an analyte detection region in fluid communication with the flow channel. The analyte detection region is provided with a binding moiety, optionally immobilized therewithin, for specifically binding the analyte. The mesoscale dimension of the detection region kinetically enhances binding of the binding moiety and the analyte. That is, in the detection region, reactants are brought close together in a confined space so that multiple molecular collisions occur. The devices may be used to implement a variety of automated, sensitive and rapid clinical tests including the analysis of cells or macromolecules, or for monitoring reactions or cell growth.

Generally, as disclosed herein, the solid substrate comprises a chip containing the mesoscale flow system. The chips are designed to exploit a combination of functional geometrical features and generally known types of clinical chemistry to implement the detection of microquantities of an analyte. The mesoscale flow system may be designed and fabricated from silicon and other solid substrates using established micromachining methods, or by molding polymeric materials. The mesoscale flow systems in the devices may be constructed by microfabricating flow channel(s) and detection region(s) into the surface of the substrate, and then adhering a cover, e.g., a transparent glass cover, over the surface. The channels and chambers in cross-section taken through the thickness of the chip may be triangular, truncated conical, square, rectangular, circular, or any other shape. The devices typically are designated on a scale suitable to analyze microvolumes (<5 µL) of sample, introduced into the flow system through an inlet port defined, e.g., by a hole communicating with the flow system through the substrate or through a transparent coverslip. Cells or other analytes present in very low concentrations (e.g. nanogram quantities) in microvolumes of a sample fluid can be rapidly analyzed (e.g., <10 minutes).

The chips typically will be used with an appliance which contains a nesting site for holding the chip, and which mates an input port on the chip with a flow line in the appliance. After biological fluid such as blood, plasma, serum, urine, sputum, saliva, or other fluids suspected to contain a particular analyte, cellular contaminant, or toxin is applied to the inlet port of the substrate, the chip is placed in the appliance and a pump is actuated to force the sample through the flow system. Alternatively, a sample may be injected into the chip by the appliance, or the sample may enter the mesoscale flow system of the chip through the inlet port by capillary action.

In the devices, the binding of an analyte to a binding moiety serves as a positive indication of the presence of the analyte in a sample. The mesoscale detection region is provided with a binding moiety capable of specifically binding to the preselected analyte. The binding moiety may be delivered to the detection region in, e.g., a solution. Alternatively, the binding moiety may be immobilized in the detection region. The internal surfaces of the mesoscale detection region of the device may be coated with an immobilized binding moiety to enable the surface to interact with a fluid sample in order to detect or separate specific fluid sample constituents. Antibodies or polynucleotide probes may be immobilized on the surface of the flow channels, enabling the use of the mesoscale flow systems for immunoassays or polynucleotide hybridization assays. The binding moiety also may comprise a ligand or receptor. A binding moiety capable of binding cells via a cell surface molecule may be utilized, to enable the isolation or detection of a cell population in a biological microsample. The mesoscale flow system may also include protrusions or a section of reduced cross sectional area to enable the sorting or lysis of cells in the microsample upon flow through the flow system.

Analyte binding to a binding moiety in the detection region may detected optically, e.g., through a transparent or translucent window, such as a transparent cover over the detection region or through a translucent section of the substrate itself. Changes in color, fluorescence, luminescence, etc., upon binding of the analyte and the binding moiety, indicating a positive assay can be detected either visually or by machine. The appliance may include sensing equipment, such as a spectrophotometer, capable of detecting changes in optical properties, due to the binding of an analyte to a binding moiety in the detection region, through a clear cover disposed over the detection region.

The device may further include means for delivering reagents such as a labeled substance to the detection region that binds to the analyte to provide a detectable signal indicative of the presence of the analyte. Optionally, depending on the protocol being exploited in the structure of the chip, the appliance also may be designed to inject reagents necessary to complete the assay, e.g., to inject a binding protein tagged with an optically detectable moiety, a substrate solution for reaction with an enzyme, or other reagents.

A positive assay may also be indicated by detectable agglutination or flow impedence upon analyte binding. The presence of a preselected analyte in a fluid sample may be detected by sensing analyte-induced changes in sample fluid flow properties, such as changes in the pressure or electrical conductivity, at different points in the flow system. In one embodiment, analyte induced restriction or blockage of flow in the mesoscale flow system, e.g., in the fractal region, may be detected by pressure detectors, e.g., in the appliance used in combination with the device. In another embodiment, analyte-induced changes in conductivity in a region of the flow system caused by introduction of a sample fluid may be readily detected through electrical conductivity sensors in contact with the flow system. For example, the presence of analyte may cause clogging of a restricted flow passage, and beyond the passage, the absence of liquid can be detected by measuring conductivity. The appliance also may include electrical contacts in the nesting region which mate with contacts integrated into the structure of the chip to, e.g., provide electrical resistance heating or cooling to a portion of the flow system, or receive electrical signals indicative of a pressure reading, conductivity, or the like, sensed in some region of the flow system to indicate (flow restriction, as a) positive indication of the presence of the analyte.

The mesoscale devices can be adapted to perform a wide range of biological or other tests. A device may include two or more separated flow systems, e.g., fed by a common inlet port, with different binding moieties in, e.g., different detection regions to enable the detection of two or more analytes simultaneously. The device may also comprise a control flow system so that data from the sample region and the control region may be detected and compared. Essentially any test involving detection of the presence or concentration of a molecular or atomic scale analyte, or the presence of a particular cell type, can be implemented to advantage in such structures. The mesoscale devices may provide a rapid chemical test for the detection of pathogenic bacteria or viruses. The devices may also provide a rapid test for the presence or concentration of blood constituents such as hormones. Other applications include but are not limited to a range of other biological assays such as blood type testing.

The devices as disclosed herein are all characterized by a mesoscale detection region containing a binding moiety that reacts with the analyte component, such as a molecular analyte or a cell type, to detect the presence or concentration of the analyte. The device may be readily sterilized prior to an assay. Assays may be completed rapidly, and at the conclusion of the assay the chip can be discarded, which advantageously prevents contamination between samples, entombs potentially hazardous material, produces only microvolumes of waste fluid for disposal, and provides an inexpensive, microsample analysis. Some of the features and benefits of the devices are summarized in Table 1.

TABLE 1

| Feature | Benefit |
|---|---|
| Flexibility | No limits to the number of chip designs or applications available. |
| Reproducible | Allows reliable, standardized, mass production of chips. |
| Low Cost Production | Allows competitive pricing with existing systems. Disposable nature for single-use processes. |
| Small Size | No bulky instrumentation required. Lends itself to portable units and systems designed for use in non-conventional lab environments. Minimal storage and shipping costs. |
| Microscale | Minimal sample and reagent volumes required. Reduces reagent costs, especially for more expensive, specialized test procedures. Allows simplified instrumentation schemes. |
| Sterility | Chips can be sterilized for use in microbiological assays and other procedures requiring clean environments. |
| Sealed System | Minimizes biohazards. Ensures process integrity. |
| Multiple Circuit Capabilities | Can perform multiple processes or analyses on a single chip. Allows panel assays. |
| Multiple Detector Capabilities | Expands capabilities for assay and process monitoring to virtually any system. Allows broad range of applications. |
| Reuseable Chips | Reduces per process cost to the user for certain applications. |

BRIEF DESCRIPTION OF THE DRAWINGS

FIG. 17b is a perspective view of the device shown in FIG. 17a.

Like reference characters in the respective drawn figures indicate corresponding parts.

DETAILED DESCRIPTION

Figure 1:
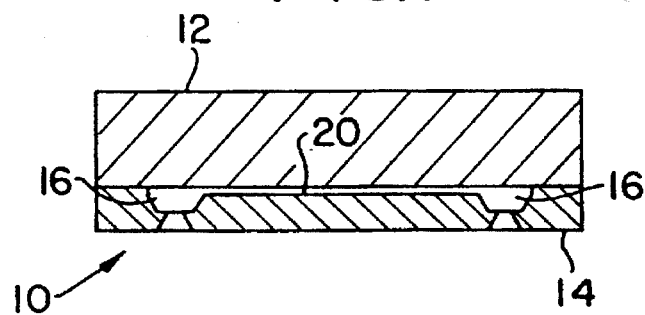
FIG. 1 is a schematic longitudinal cross sectional view of a device according to the invention that includes a solid substrate 14, on which are machined entry ports 16 connected by mesoscale flow channel 20, with a transparent cover 12 adhered to the surface of the substrate.

The invention provides a family of small, mass produced, typically one-use devices for detecting a particular analyte in a fluid microsample. The device comprises a solid substrate, typically on the order of a few millimeters thick and approximately 0.2 to 2.0 centimeters square, that is microfabricated to define a sample inlet port and a mesoscale flow system. The mesoscale flow system includes at least one sample flow channel extending from the inlet port and at least one analyte binding region in fluid communication with the flow channel which contains a binding moiety for specifically binding the analyte. Optionally the binding moiety may be immobilized within the binding region. As disclosed herein, mesoscale detection systems may be used in a wide range of rapid tests, including the analysis of cells or macromolecules, or for monitoring reactions or cell culture growth. The devices may be fabricated with two or more mesoscale flow systems which comprise two or more different binding regions containing binding moieties for different analytes, allowing two or more assays to be conducted simultaneously. At the conclusion of the assay the devices typically are discarded.

Mesoscale devices having flow channels and chambers with at least one mesoscale dimension can be designed and fabricated in large quantities from a solid substrate material. Silicon is preferred because of the enormous body of technology permitting its precise and efficient fabrication, but other materials may be used including polymers such as polytetrafluoroethylenes. The sample inlet port, the mesoscale flow system, including the sample flow channel(s) and the analyte detection region(s), and other functional elements thus may be fabricated inexpensively in large quantities from a silicon substrate by any of a variety of micromachining methods known to those skilled in the art. The micromachining methods available include film deposition processes such as spin coating and chemical vapor deposition, laser fabrication or photolithographic techniques such as UV or X-ray processes, or etching methods including wet chemical processes or plasma processes. (See, e.g., Manz et al., *Trends in Analytical Chemistry* 10:144–149 (1991)). Flow channels of varying widths and depths can be fabricated with mesoscale dimensions, i.e., with cross-sectional dimensions on the order of 0.1 to 500 µm.

The silicon substrate containing a fabricated mesoscale flow channel may be covered and sealed with a thin anodically bonded glass cover. Other clear or opaque cover materials may be used. Alternatively, two silicon substrates can be sandwiched, or a silicon substrate may be sandwiched between two glass covers. The use of a transparent cover results in a window which facilitates dynamic viewing of the channel contents and allows optical probing of the detection region either visually or by machine. Other fabrication approaches may be used. In one embodiment, electron micrographs of biological structures such as circulatory networks may be used as masks for fabricating mesoscale flow systems on the substrate. Mesoscale flow systems may be fabricated in a range of sizes and conformations.

Figure 2:
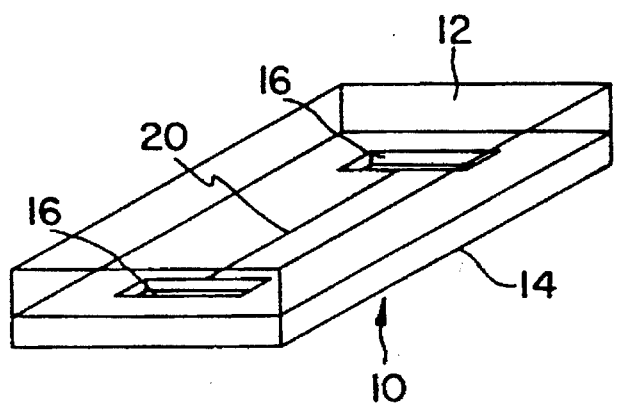
FIG. 2 is a perspective view of the device of FIG. 1.
Figure 3:
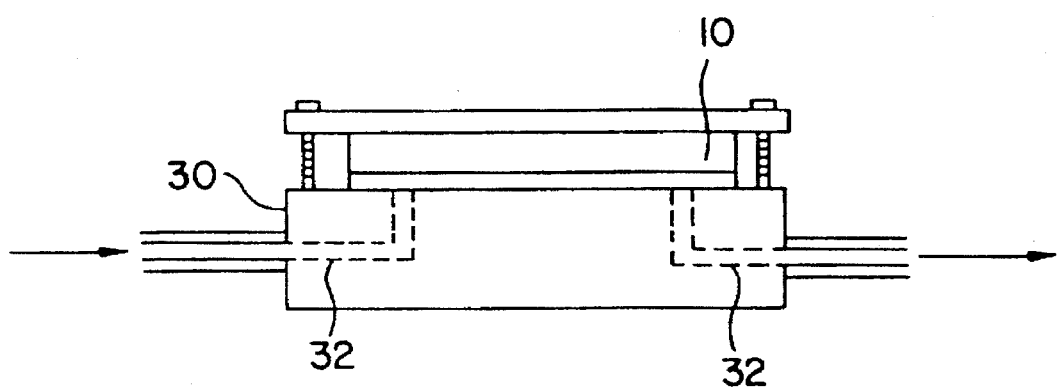
FIG. 3 is a cross sectional view of a support block 30 for holding device 10 that includes ports 32 for delivery or removal of reagents or sample fluids from device 10.

In one embodiment, illustrated schematically in FIGS. 1 and 2, the device 10 may include a silicon substrate 14 microfabricated with a mesoscale flow channel 20, which, in this instance, also serves as a detection region, and which may be provided with binding moieties capable of binding a preselected analyte. Sample or reagent fluid may be added or recovered from flow channel 20 via ports 16 which are fabricated on either end of the flow channel 20. The substrate 14 is covered with a glass or plastic window 12. During an analysis, the device 10 may be placed in support structure 30 (FIG. 3), which is provided with internal flow paths 32 for delivery and recovery of sample fluid through the inlet ports of device 10. The dimensions of the microchannels in the silicon mesoscale devices may vary in the range from approximately 2.0 µm–500 µm wide and approximately 0.1 µm–500 µm in depth, a range comparable to cellular or macromolecular dimensions, where fluid motion of multiphasic materials such as fluid and cell culture medium has not been systemically investigated. The inlet ports on the devices may be microfabricated with mesoscale or, alternatively, larger dimensions.

The capacity of the devices is very small and therefore reduces the amount of sample fluid required for an analysis. For example, in a 1 cm×1 cm silicon substrate, having on its surface an array of 500 grooves which are 10 microns wide×10 microns deep ×1 cm ($10^4$ microns) long, the volume of each groove is $10^{-3}$ µL and the total volume of the 500 grooves is 0.5 µL. The low volume of the mesoscale flow systems enhances the reaction rates of assays conducted in the devices. For example, in a mesoscale detection chamber containing a surface coating of an immobilized binding moiety, as predicted by the Law of Mass Action, as the volume of the mesoscale detection chamber decreases, the surface area to volume ratio of the binding moiety in the detection region increases, which results in an increased rate of intermolecular reaction between the analyte and the binding moiety. The entire mesoscale flow systems of devices of the invention typically have volumes on the order of less than 10 µL. Detection chambers are small enough in at least one dimension to favor fast kinetics. The mesoscale flow systems in the devices may be microfabricated with microliter volumes, or alternatively nanoliter volumes or less, which advantageously limits the amount of sample and/or reagent fluids required for an assay.

Figure 5:
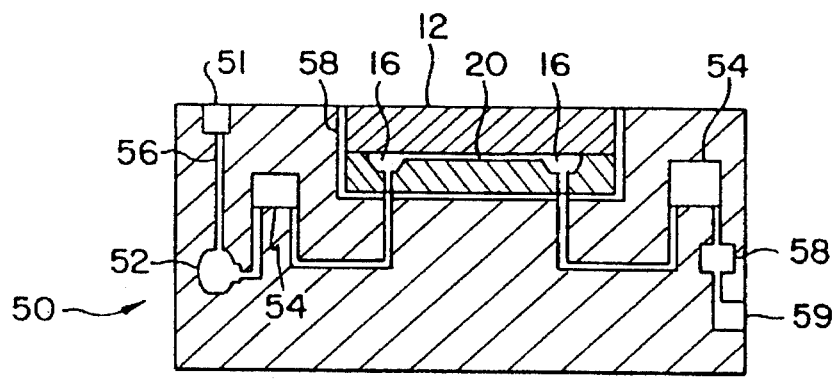
FIG. 5 is a schematic illustration of analytical device 10 nested within appliance 50, which is used to support the device 10 and to regulate and detect the pressure of sample fluids in device 10.

The analytical devices containing the mesoscale flow system can be used in combination with an appliance for delivering and receiving fluids to and from the devices, such as appliance 50, shown schematically in FIG. 5, which incorporates a nesting site 58 for holding the device 10, and for registering ports, e.g., ports 16 on the device 10, with a flow line 56 in the appliance. The appliance may include means, such as pump 52 shown in FIG. 5, for forcing the sample through the flow system. After a biological fluid sample suspected to contain a particular analyte is applied to the inlet port 51 of the appliance, pump 52 is actuated to force the sample into port 16 of device 10 and the mesoscale flow channel 20. Alternatively a sample may be injected into the chip by the appliance, or the sample may enter the mesoscale flow system of the device through the inlet port by capillary action. In another embodiment, the appliance may be disposed over the substrate, and may be provided with a flow line communicating with the inlet ports in the device, e.g., in the absence of a cover over the device, to enable a sample to be injected via the appliance into the device. Other embodiments of appliances may be fabricated in accordance with the invention for use in different assay protocols with different devices. The flow systems of the devices may be filled to a hydraulically full volume and the appliance may be utilized to direct the flow of fluid through the flow system, e.g., by means of valves located in the device or in the appliance.

Figure 20:
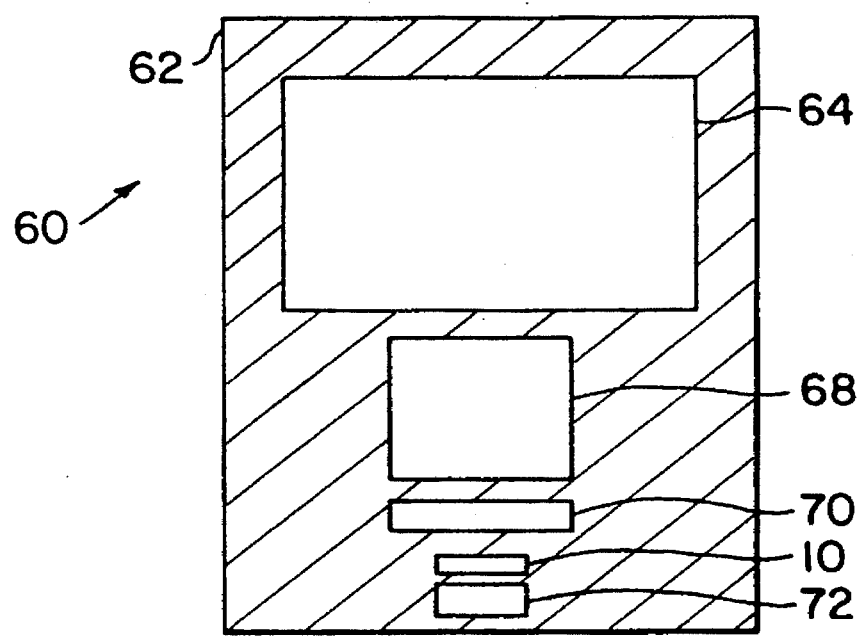
FIG. 20 is a schematic cross sectional view of the apparatus 60 of FIG. 19.
Figure 19:
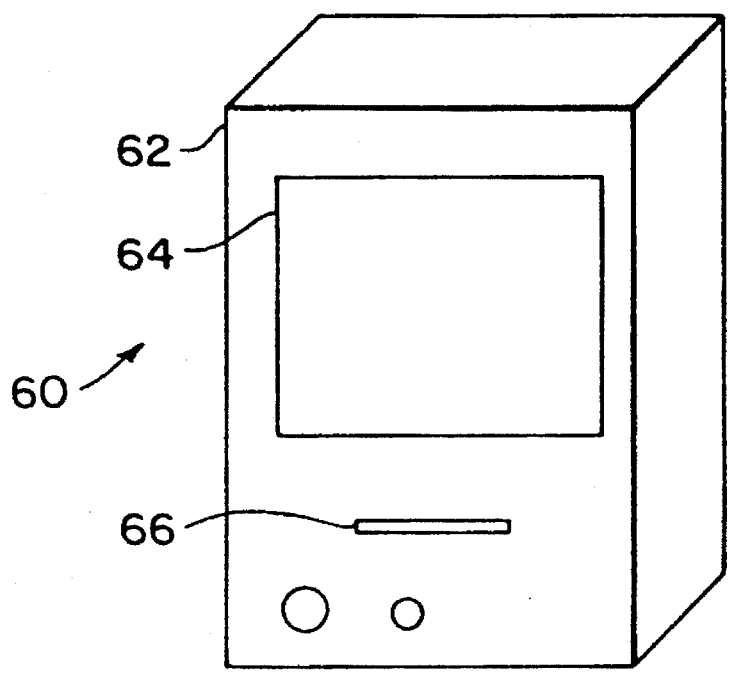
FIG. 19 is a schematic perspective view of an apparatus 60 used in combination with device 10 for viewing the contents of device 10.

The analytical devices also may be utilized in combination with an appliance for viewing the contents of the mesoscale channels in the devices. The appliance in one embodiment may comprise a microscope for viewing the contents of the mesoscale channels in the devices. In another embodiment, a camera may be included in the appliance, as illustrated in the appliance 60 shown schematically in FIGS. 19 and 20. The appliance 60 is provided with a housing 62, a viewing screen 64 and a slot 66 for inserting a chip into the appliance. As shown in cross section in FIG. 20, the appliance 60 also includes a video camera 68, an optical system 70, and a tilt mechanism 72 for holding device 10, and allowing the placement and angle of device 10 to be adjusted manually. The optical system 70 may include a lens system for magnifying the channel contents, as well as a light source. The video camera 68 and screen 64 allow analyte induced changes in sample fluid properties, such as flow properties or color, to be monitored visually, and optionally recorded using the appliance.

Binding moieties may be introduced into the mesoscale binding region in a solution via an inlet port in fluid communication with the binding region. Alternatively, binding moieties may be immobilized in the mesoscale binding region of the analytical devices after its manufacture by, for example, physical absorption or chemical attachment to the surface of the flow system or to a solid phase reactant such as a polymeric bead disposed in the binding region.

The surfaces of the mesoscale detection channels in the silicon substrates can be chemically activated and reacted with a protein, lipid, polysaccharide or other macromolecule to form a coated surface in the mesoscale flow channels. Techniques for the chemical activation of silaceous surfaces are available in the art. (See, e.g., Hallet in: *Solid Phase Biochemistry*, W. H. Scouten, Ed., John Wiley, New York, pp 535–597 (1983); and Mandenius et al., *Anal. Biochem.*, 137:106–114 (1984) and 170:68–72 (1988) and Mandenius et al., *Methods in Enzymology*, 137: 388–394). There are a number of techniques in the art for attaching biomolecules to silicon. For example, enzymes may be immobilized on silicon devices via entrapment in a photo-crosslinkable polyvinyl alcohol (Howe et al., *IEEE Transactions Electron Devices*, ED33:499–506 (1986) or attached indirectly using preformed membranes (Hanazato et al., *IEEE Transactions Electron Devices*, ED33:47–51 (1986). A hydrophobic bilayer glycerol monooleate coating may be fabricated on a silicon substrate. Fromherz et al., *Biochim. Biophys. Acta*, 1062:103–107 (1991).

Protein conjugation and immobilization techniques known in the art may be adapted for use with activated silaceous surfaces. Kennedy et al., *Clin. Chem. Acta*, 70:1–31 (1976); Sankolli et al., *J. Imm. Methods*, 104:191–194 (1987); Kricka et al., *Clin. Chem.*, 26:741–744 (1980); and DeLuca et al., *Arch. Biochem. Biophys.*, 225:285–291 (1983). Known chemistries in the art may be adapted for use in attaching biomolecules to coated or uncoated silicon channel surfaces. A binding moiety such as an antigen binding protein, a polynucleotide probe, or one of a ligand/receptor pair may be attached to the silicon channel surfaces. The surface coated mesoscale flow systems can be utilized in any of a wide range of available binding assays known in the art such as immunoassays, enzymatic assays, ligand/binder assays, polynucleotide hybridization assays, and cell surface binding assays. The detection of cellular or macromolecular analytes can be implemented by selecting the appropriate binding moiety coated on the surface of the detection region.

In addition, magnetic beads may be utilized in the device, which can be moved through the mesoscale flow system using an externally applied magnetic field, e.g., from a magnetic source located in an appliance utilized in combination with the device. The binding moiety or other reagent required in an assay may be immobilized on a magnetic bead to enable, e.g., the delivery of the binding moiety to the detection region to bind to the analyte. After the binding of the analyte to the binding moiety attached to the magnetic bead, the analyte may be, e.g., further purified, or moved via an external magnetic field to a different detection region in the flow system for further analyses.

The binding of the analyte to the binding moiety in the binding region can be detected by any of a number of methods including monitoring the pressure or electrical conductivity of sample fluids in the device as disclosed herein or by optical detection through a transparent cover either visually or by machine. Devices such as valves, mesoscale pressure sensors, and other mechanical sensors can be directly fabricated on the silicon substrate and can be mass-produced according to well established technologies. Angell et al., *Scientific American* 248:44–55 (1983).

The binding of an analyte to a binding moiety in the binding region can be detected optically. The simplest embodiment is one in which a positive result is indicated by an agglomeration or agglutination of particles, or development of or change in color, which can be visually observed, optimally with the aid of a microscope. The optical binding of the binding of an analyte to a binding moiety in the mesoscale binding chambers can be implemented by the attachment of a detectable label, such as a fluorescent or luminescent molecule or polymeric support, such as a bead, to either the analyte or the binding moiety using assay protocols known per se. The luminescent or fluorescent label in the binding region can be detected by light microscopy through a translucent window disposed over the substrate. Analytes may be detected by a luminescent or fluorescent signal produced by a binding moiety upon binding of the analyte. Alternatively, a second labelled substance, such as a fluorescent labelled antibody can be delivered through the flow system to bind to the bound analyte/binding moiety complex in the binding region to produce a "sandwich" including an optically detectable moiety whose presence is indicative of the presence of the analyte. For example, immunogold or immunofluorescent labels reported in the prior art may be utilized. (See, e.g., Rosenberg et al., *Clin. Chem.* 30:1462–1466 (1984); Rosenberg et al., *Clin. Chem.* 31:1444–1448 (1985); and Goin et al., *Clin. Chem.* 32:1655–1659 (1986)).

Figure 17B:
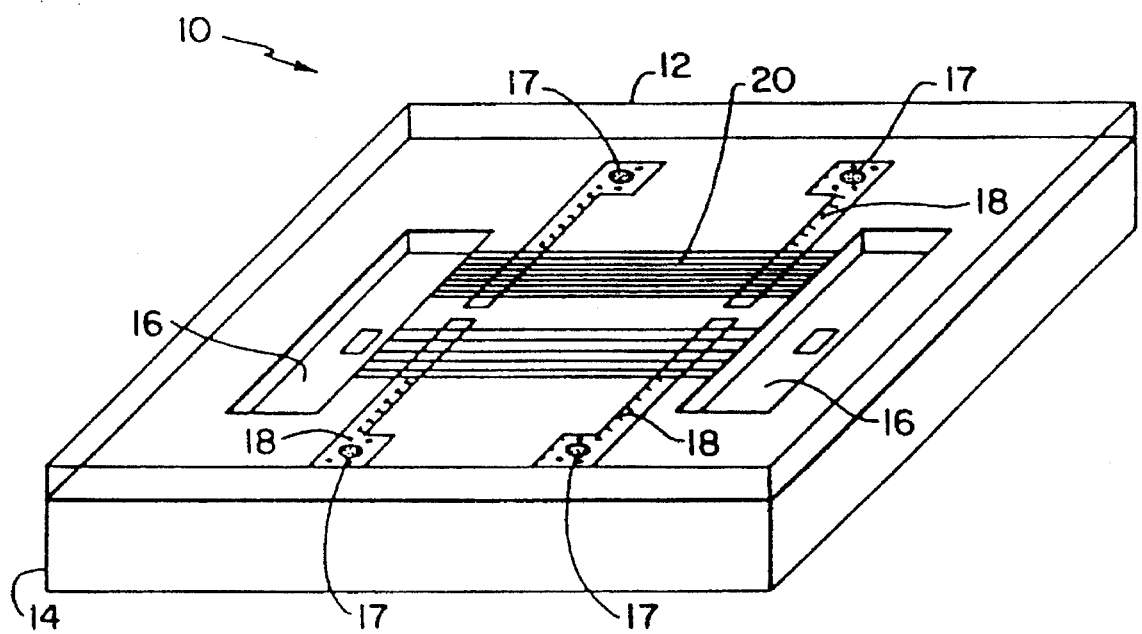
Figure 17A:
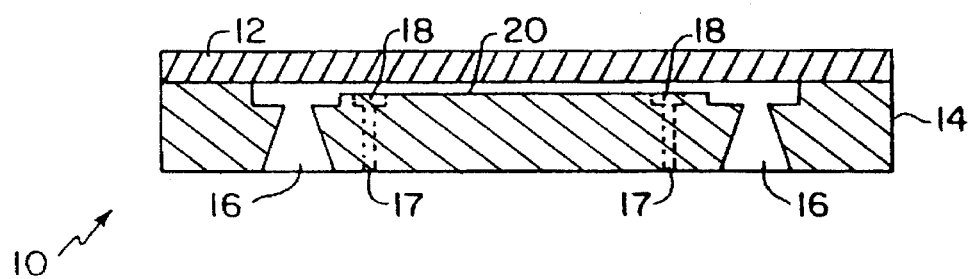
FIG. 17a is a schematic longitudinal cross sectional view of a device according to the invention which includes electrical contacts 17 and 18 for measuring conductivity of fluids in the device.

The binding of an analyte in a liquid biological fluid sample to a binding moiety in the detection region also may be detected by sensing electrical conductivity at some region within the device. The conductivity of liquid in the mesoscale flow paths can be measured in order to detect changes in electrical properties upon analyte binding to binding moieties in the detection region. The conductivity may be measured, e.g., in the device 10 shown schematically in FIGS. 17a and 17b. Device 10 includes the silicon substrate 14 on which are microfabricated inlet ports 16 and flow channel 20. The substrate is covered by a translucent window 12. Electrical conductivity measurements are made using the electrical contacts 18 which are fabricated on the top side of the substrate in contact with the mesoscale sample flow channel 20, and which are connected to contacts 17 which extend through to the bottom of the substrate. The contacts 17 can be fabricated by known techniques of thermal gradient zone melting. (See Zemel et al., in: *Fundamentals and applications of Chemical Sensors*, D. Schuetzle and R. Hammerle, Eds., ACS Symposium Series 309, Washington, DC, 1986, p. 2.) Device 10 may be nested in an appliance such as appliance 50, shown in FIG. 5, capable of detecting conductivity changes through the contacts 17. Changes in conductivity can be correlated with changes in fluid properties, such as fluid pressure, induced by analyte binding in the binding region.

The binding of an analyte to a binding moiety in the binding region also can be detected by monitoring the pressure of the sample fluids in certain specially designed regions of the mesoscale flow passages. For example, a pressure detector connected to sample fluid entering and exiting the mesoscale flow system will allow the binding of pressure decreases caused by analyte binding and resulting clogging or flow restriction. FIG. 5 shows schematically, as an example, device 10, which is nested within appliance 50, which includes two pressure detectors 54 for detecting flow pressure of fluids entering and exiting device 10 through ports 16. When, during an assay, particles agglomerate or molecules chemically interact to form a network clogging the flow passage or increasing the viscosity of the liquid, that change can be detected as a pressure change indicative as a positive result. A mesoscale pressure sensor also may be fabricated directly on the silicon substrate. Angell et al., *Scientific American* 248:44-55 (1983).

Figure 4:
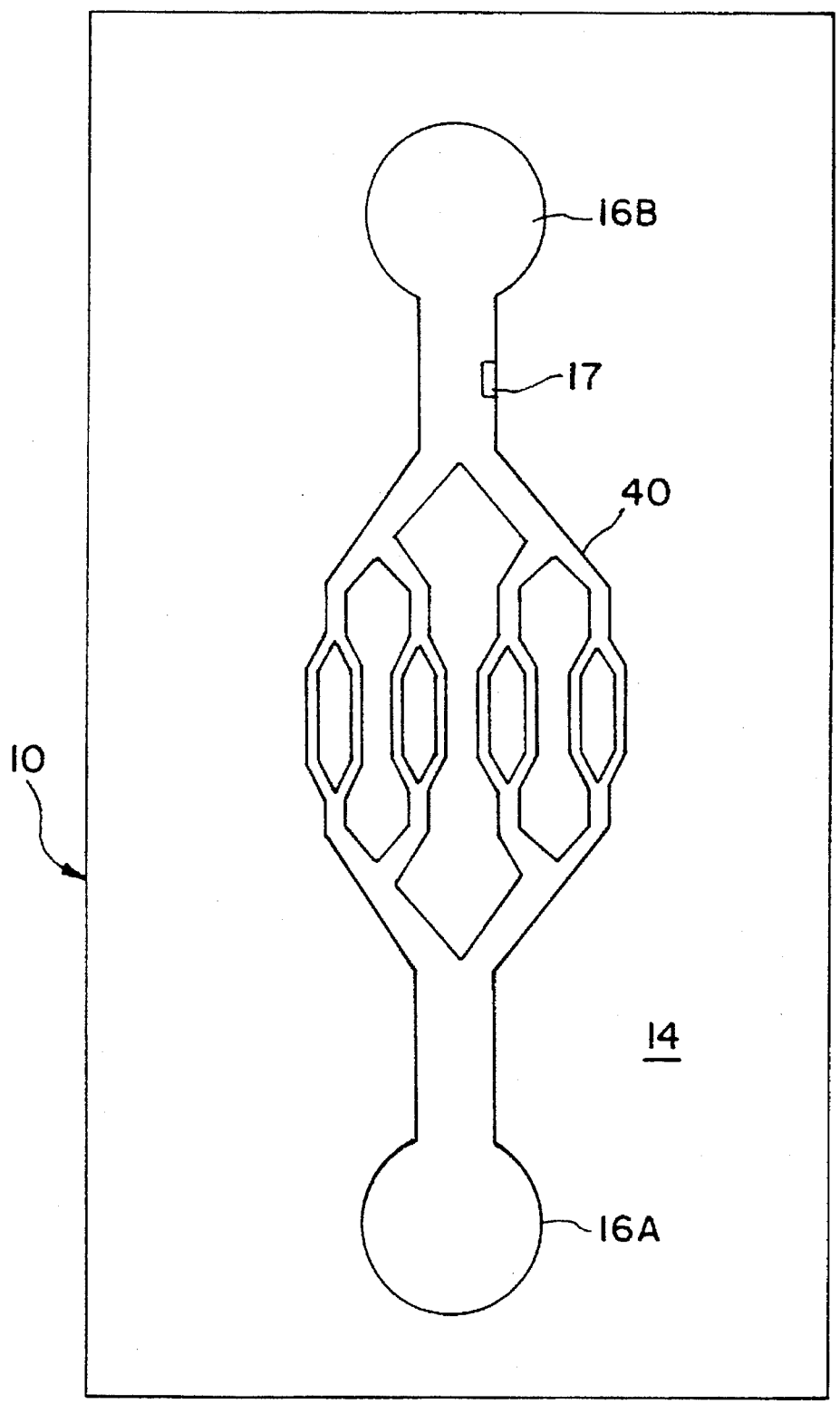
FIG. 4 is a schematic plan view of a substrate 14 fabricated with a fractally bifurcating system of flow channels 40 symmetrically disposed on the substrate.
Figure 18:
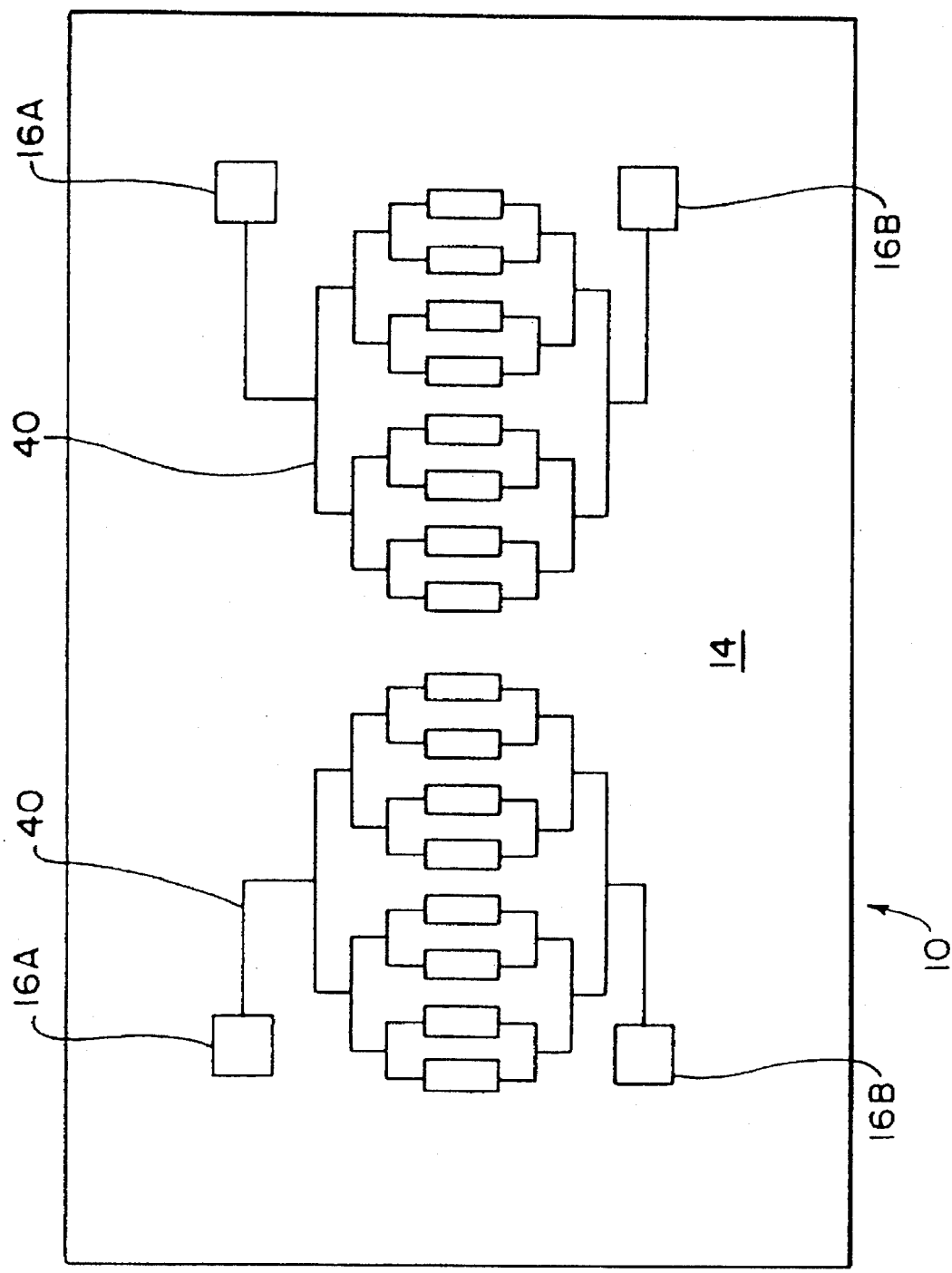
FIG. 18 is a schematic plan view of a substrate microfabricated with a pair of fractally bifurcating flow channels 40.

This form of binding of an analyte binding to a binding moiety in the binding region can be enhanced by geometries sensitive to flow restriction in the flow system. In one embodiment, the mesoscale flow channels in the devices may be constructed with a "fractal" pattern, i.e., of a pattern of serially bifurcating flow channels. FIG. 18 illustrates schematically one embodiment of a device 10 which includes substrate 14 microfabricated with two fractal flow systems 40. The fractally bifurcating channels may be fabricated on a silicon substrate with reduced dimensions at each bifurcation, providing sequentially narrower flow channels, as illustrated schematically in FIG. 4. FIG. 4 shows a schematic plan view of a substrate 14 fabricated with a fractally bifurcating system of flow channels 40 connected to ports 16. The channels in this embodiment are symmetrically disposed and have a sequentially narrower diameter towards the center of the substrate. Fluid flow in these fractally constructed flow systems is very sensitive to fluid viscosity and to the development of flow restriction caused, for example, by the proliferation of cells, or the agglomeration of cells, particles, or macromolecular complexes that may be present in a sample. The binding of the presence of an analyte based on flow restriction is described in U.S. application Ser. No. 07/877,701, the disclosure of which is incorporated herein by reference.

The fractally designed microchannels readily allow, e.g., the growth of organisms in a culture to be monitored on the basis of flow impedance due to changes in fluid viscosity which can be detected, e.g., optically through a transparent cover over the substrate. The presence and growth of an organism in a sample will influence the flow characteristics within the fractal. One or more pressure sensors may be utilized to detect pressure changes due to changes in fluid properties caused by the presence of an analyte in or beyond the fractal flow paths. Changes in conductivity upon analyte binding also may be readily detected through electrical conductivity sensors in contact with the flow region. For example, clogging of the fractal region 40 of device 10 in FIG. 4, which blocks flow of analyte from input port 16A to outlet port 16B may be detected by a conventional conductivity probe 17, whose output is indicative of the presence or absence of aqueous fluid in the outflow channel. Binding moieties may be provided in fractal region, e.g., immobilized on the surface of the fractal flow path, or on a solid phase reactant such as a bead, to bind to the analyte and enhance flow restriction in the fractal flow path.

A large number of binding assay protocols known in the art may be exploited in the mesoscale binding systems of the invention.

The reaction of an analyte with a binding moiety in the binding region may be detected by means of an agglutination. A fluorescent or luminescent labelled molecule or bead capable of binding to the analyte or analyte/binding moiety complex in the binding region may be used to enable the binding of agglutination of the binding moiety and the analyte by light microscopy through a translucent cover over the binding region. For example, the agglutination of blood cells in a mesoscale binding chamber can serve as a positive test for the blood type of the sample. Antibodies may be coated, either chemically or by absorption, on the surface of the binding region to induce agglutination, giving a positive test for blood type. The blood sample may be mixed with a fluorescent dye to label the blood cells and to enable the optical binding of the agglutination reaction. Antibodies bound to fluorescent beads also may be utilized. A plurality of binding regions housing different antibodies may be fabricated in the mesoscale flow paths to allow the simultaneous assay of e.g., A, B and Rh blood types in one device.

Figure 10A:
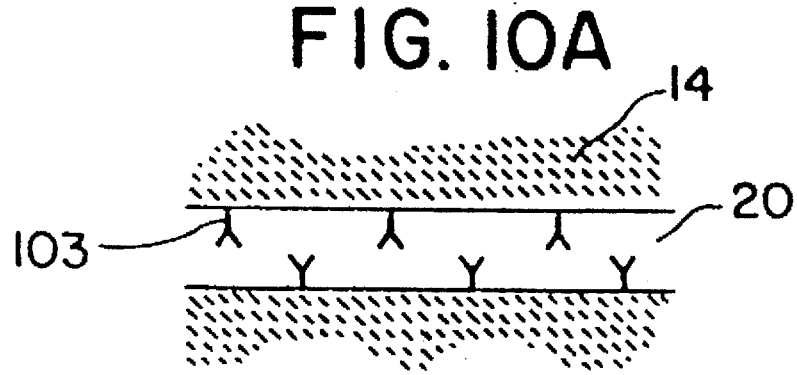
FIGS. 10A–D are schematic illustrations of a cross-section of a portion of a mesoscale flow channel 20 within a substrate 14, on which antibodies 103 are immobilized, and illustrating changing states of the system during an analysis.
Figure 10B:
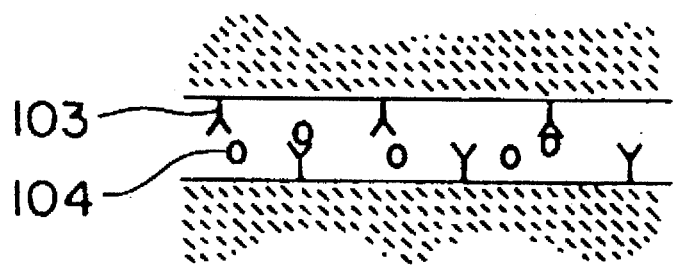
Figure 10C:
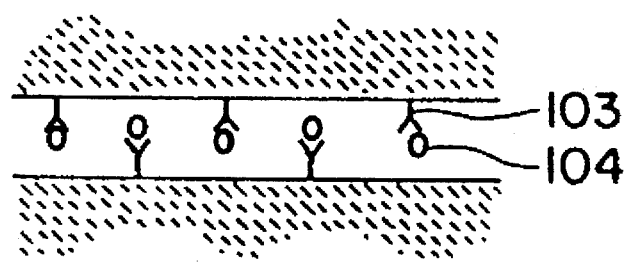
Figure 10D:
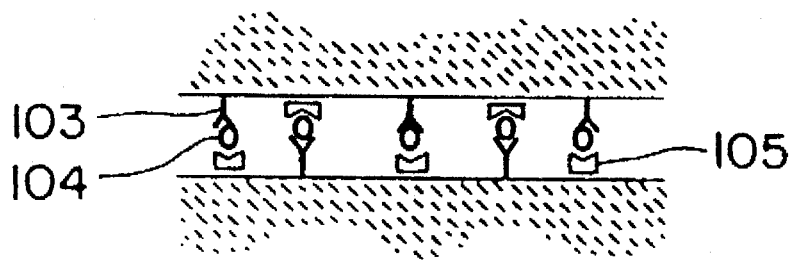
Figure 11A:
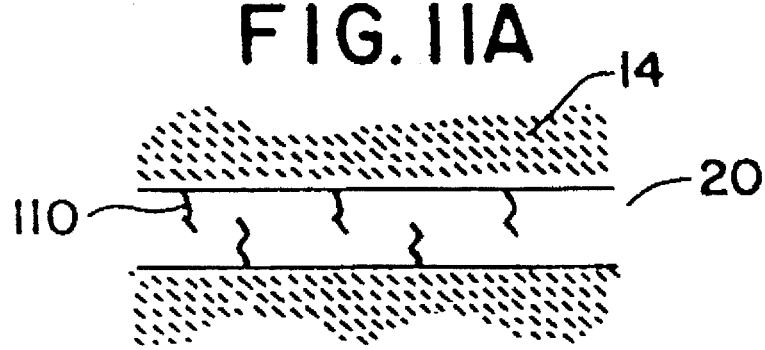
FIGS. 11A–D are schematic illustrations of a cross-section of a portion of a mesoscale flow channel 20 within a substrate 14, on which DNA binding probes 110 are immobilized, and illustrating changing states of the system during an analysis.
Figure 11B:
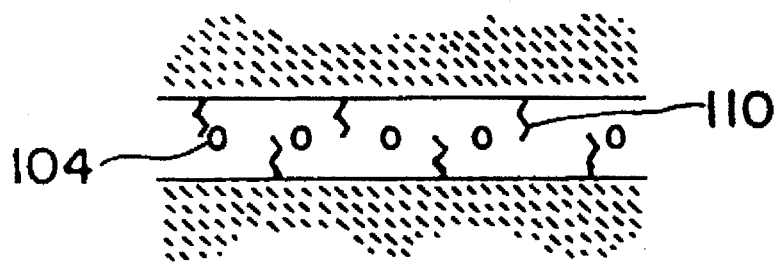
Figure 11C:
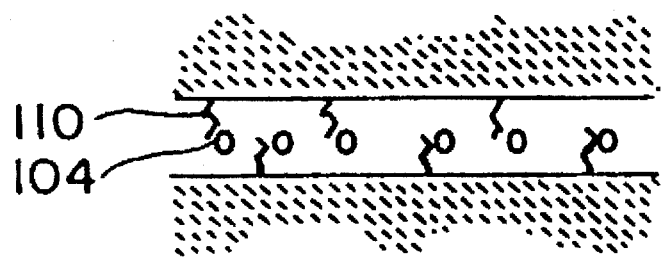
Figure 11D:
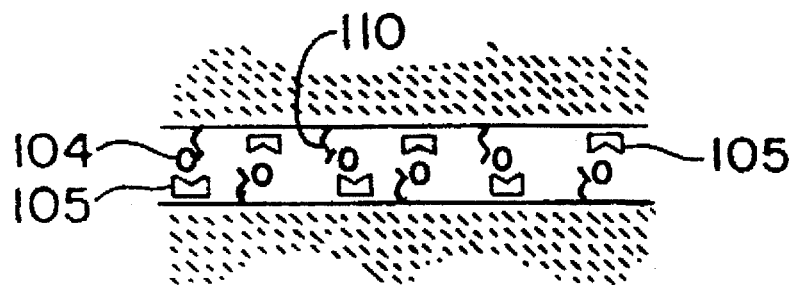

Immunochemical assay techniques known in the art, such as antibody sandwich assays and enzyme-linked immunoassays, may be exploited in the mesoscale binding regions of the devices to detect a preselected analyte. (See Bolton et al., *Handbook of Experimental Immunology*, Weir, D. M., Ed., Blackwell Scientific Publications, Oxford, 1986, vol. 1, Chapter 26, for a general discussion on immunoassays.) In one embodiment, the analyte may be an antigen and the binding moiety may be a labelled antigen binding protein, e.g. a fluorescent labelled antibody. Alternatively a sandwich immunoassay can be performed wherein a tagged binding molecule, such as a fluorescent labelled antibody, is utilized to detectably bind to an analyte/binding moiety complex formed in the binding region. An example of a sandwich immunoassay is illustrated schematically in FIGS. 10A–D, wherein the surface of mesoscale flow channel 20 in substrate 14 is coated with an antibody 103 capable of binding an analyte 104. FIGS. 10B and 10C illustrate the binding of the analyte 104 to the antibody 103 in the flow channel. Bound analyte is then detected by the subsequent addition of a fluorescent labelled antibody 105 which complexes to the bound analyte as illustrated in FIG. 10D. The fluorescent labelled complex can be detected through a translucent window over the binding region using a fluorometer.

Luminescence may be readily detected in the mesoscale flow systems of the devices, emitted from, e.g., a fluorescein labeled binding moiety. In one embodiment, luminescence emission may be readily detected in a mesoscale flow system, e.g., using a microplate reader, including a photomultiplier tube, or a camera luminometer. In one embodiment, the analyte may be detected by the use of a binding moiety comprising two antibodies capable of binding to the analyte, wherein one antibody is labeled with fluorescein, which emits light, and a second antibody is labeled with rhodamine, which absorbs light. When the rhodamine and fluorescein-labeled antibodies each bind to the analyte, a quenching of the fluorescein can be observed, indicating the presence of the analyte. Nakamura et al., eds., *Immunochemical Assays and Biosensor Technology for the 1990s*, American Society of Microbiology, Washington, D.C., pp. 205–215. In one embodiment, the fluorescein labeled antibody is immobilized in the binding region. The analyte and the rhodamine-labeled antibody are then delivered to the binding region, and quenching of the fluorescein is observed indicating the presence of the analyte. In another embodiment, fluorescein-labeled antibodies conjugated to and coating a bacterial magnetic particle may be utilized in an immunoassay, wherein the antibody is capable of binding to the analyte. Nakamura et al. *Anal. Chem.* 63:268–272 (1991). In this embodiment, the agglutination of bacterial magnetic particles conjugated to the fluorescein-labeled antibody causes a fluorescence quenching, indicating a positive assay for the analyte. The agglutination and resulting quenching may be enhanced by applying a magnetic field to the mesoscale binding region, e.g., via a magnetic source located in an appliance used in combination with the appliance.

In another embodiment, polynucleotide hybridization assays known in the art may be performed (Maniatis et al., *Molecular Cloning: A Laboratory Manual*, 2nd ed., Cold Spring Harbor Press, 1989). As illustrated schematically in FIG. 11, the surface of flow channel 20 in substrate 14 may be coated with a polynucleotide probe 110. Upon binding of the complementary analyte polynucleotide 104 to the immobilized polynucleotide probe 110, a second detectable, e.g., fluorescent labelled, macromolecular probe 105 can be added to bind to the sample polynucleotide. Detection of fluorescence indicates a positive assay.

In other embodiments, the mesoscale flow system may include a chamber for separating a selected cell population from a biological fluid sample in preparation for downstream analysis of either a macromolecule on or within the cells or of a component in the extracellular fluid. The mesoscale separating region includes immobilized binding moieties capable of reversibly binding a target cell via a characteristic cell surface molecule such as protein. The mesoscale dimension of the separation region kinetically enhances binding of the cell and the binding moiety. In one embodiment, the cells remain immobilized while extracellular fluid flows downstream and is analyzed. In another, flow may be continued to wash the cells, e.g., with a flow of buffer. At higher flow rates and pressures, the washed cells are released from the separation region and move downstream for analysis.

Figure 13:
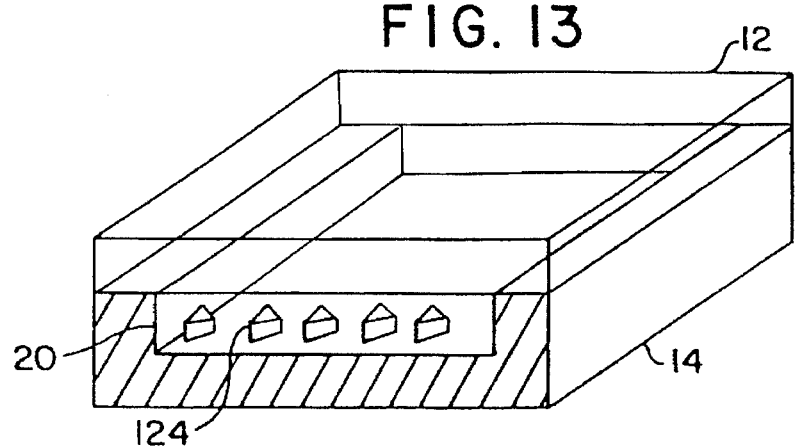
FIG. 13 is a cross sectional view of a flow channel 20 on the inert substrate 14 with cell piercing protrusions 124 extending from a wall of the channel.

The devices of the invention also may include cell lysing means in fluid communication with the mesoscale flow channel to allow the cells to be lysed prior to analysis for an intracellular molecule such as an mRNA. As illustrated in FIG. 13, the cell lysing means may comprise cell membrane piercing protrusions 124 extending from a surface of a flow channel 20. As fluid flow is forced through the piercing protrusion 124, cells are ruptured. Cell debris may be filtered off and intracellular analytes may then be analyzed. Sharp edged pieces of a material such as silicon also may be utilized, trapped with the mesoscale flow system to implement lysis of cells upon the applications of sufficient flow pressure. In another embodiment, the flow channel may simply comprise a region of restricted cross-sectional dimension which implements cell lysis upon application of sufficient flow pressure. These devices typically are used in connection with an appliance which includes means, such as a pump, for forcing the cell containing sample into the cell lysis means to cause cell lysis upon application of sufficient flow pressure. In addition, the cell lysis means may comprise a cell lysis agent. Cell lysing agents known in the art may be utilized.

Figure 12:
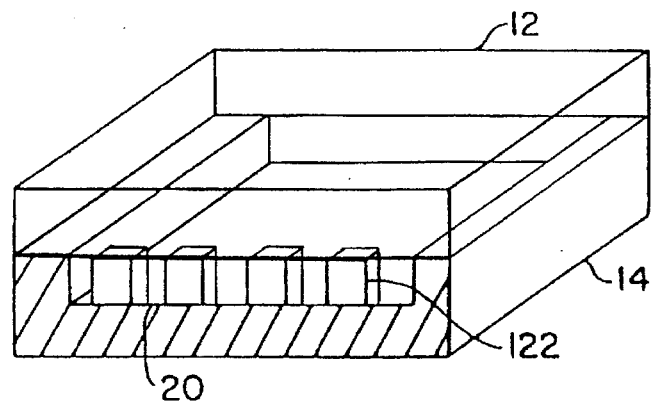
FIG. 12 is a cross sectional perspective view of a flow channel 20 on the inert substrate 14 with cell or debris filtering protrusions 122 extending from a wall of the flow channel.

As illustrated in FIG. 12, the surface of a flow channel 20 may also include protrusions 122 constituting a cellular sieve for separating cells by size. As cell samples are flowed, typically under low pressure, through the flow channel, only cells capable of passing between the protrusions 122 are permitted to flow through in the flow channel.

The mesoscale devices also may be utilized to implement enzymatic reactions. Mesoscale enzyme reaction chambers fabricated in the substrate may be temperature controlled to provide optimal temperatures for enzyme reactions. Inlet ports may be provided, in fluid communication with the enzyme reaction chamber, to allow reagents and other required enzyme assay components to be added or removed.

The assay devices embodying such chambers may be nested in an appliance such as appliance 50, illustrated schematically in FIG. 5, having means to regulate the temperature of the enzyme reaction chambers and to deliver or recover assay components through flow channels 56 in appliance 50 and ports 16 in device 10. The appliance may be utilized to implement the timed addition of sample or reagent fluids to the devices. In order to regulate the temperature of the reaction chambers, the devices may be utilized in a nesting site in an appliance utilized in combination with the device. An electrical heating or cooling element may be provided in the nesting site for heating or cooling the reaction chamber in the device. Alternatively, electrical contacts may be provided in the substrate and may be mated with electrical contacts in the appliance to provide electrical resistance heating or cooling of the reaction chamber.

Figure 15:
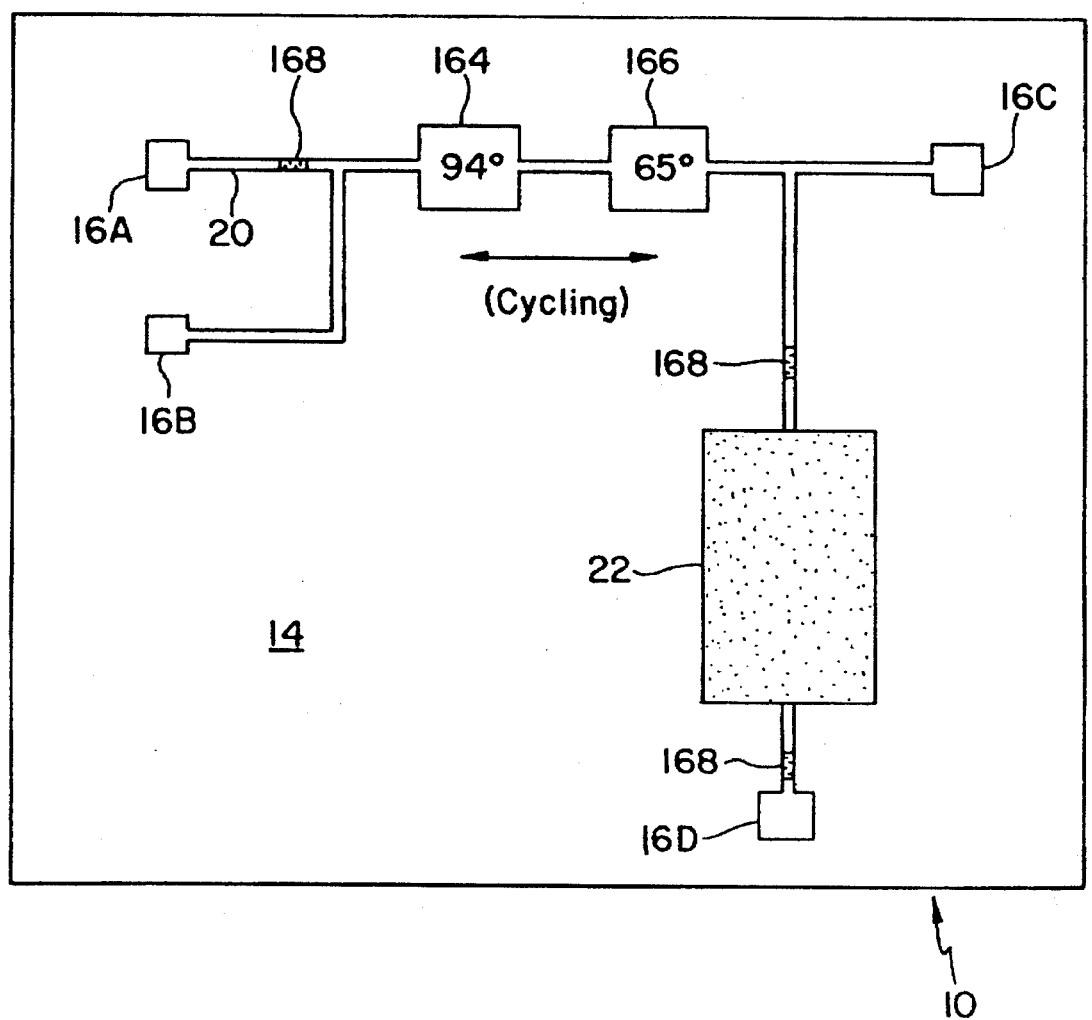
FIG. 15 is a schematic plan view of a mesoscale PCR analytical device constructed in accordance with the invention.

In one embodiment, polymerase chain reaction (PCR) may be performed in a mesoscale reaction chamber to enable the binding of a polynucleotide in a sample. Inlet ports in fluid communication with the reaction chambers permit addition of required reagents, such as nucleic acids, primers and Taq polymerase. The chain reaction may be performed, according to methods established in the art (Maniatis et al., *Molecular Cloning: A Laboratory Manual*, Cold Spring Harbor Laboratory Press, 1989). One embodiment, illustrated in FIG. 15, is PCR chip 10 which contains a pair of mesoscale PCR reaction chambers 164 and 166, microfabricated in a silicon substrate 14. A solution containing the polynucleotide to be amplified is delivered from inlet 16A through flow path 20 to the reaction chambers 164 and 166, which are heated, e.g., electrically, to 94° C. and 65° C., respectively. A pump is attached via port 16B to enable cycling of fluid between chamber 164, where polynucleotide dehybridization occurs, and chamber 166, where polymerization occurs. Port 16C can be used to vent the system, and also optionally to deliver Taq polymerase, nucleoside triphosphates, primers, and other reagents required for the polymerase reaction. A binding chamber 22 is provided in the mesoscale flow system, containing a labelled binding moiety, such as a labeled polynucleotide probe immobilized on a bead, to detect the presence of the amplified polynucleotide product.

In operation, the PCR chip 10 is used in combination with an appliance, such as appliance 50, shown in FIG. 5, which contains a nesting site for holding the chip. The appliance 50 is provided with flow paths 56 mated to ports 16A–D. The appliance also includes valves that allow the ports 16A–D to be mechanically opened and closed. The appliance 50 is used to deliver a biological sample fluid to inlet port 16A through filter 168 to reaction chambers 164 and 166. Reagents such as primers, nucleoside triphosphates, and Taq polymerase may be added to the polynucleotide sample before delivery through inlet port 16A, or optionally, reagents may be delivered to the sample in sample chambers 164 and 166 via port 16C by means of the appliance. After delivery of a sample to PCR reaction chambers 164 and 166, the appliance is utilized to shut ports 16A and 16D. Port 16C remains open as a vent. A pump disposed in appliance 50 is then utilized to cycle fluid between chamber 164, heated to 94° C., for polynucleotide dehybridization, and chamber 166, heated to 65° C., for the polymerization reaction.

The temperature of chambers 164 and 166 can be controlled by means of, e.g., an electrical contact integrated in the substrate below the reaction chambers, which can mate with electrical contacts in the appliance. Alternatively, an optical laser may be used to heat the reaction chambers, e.g., through a glass cover disposed over the substrate, or through a translucent region of the substrate itself. When the polymerase cycling reaction is complete, ports 16A and 16C are closed, port 16D is opened, and the reaction products are delivered to binding chamber 22, which contains a labeled polynucleotide probe, e.g., a probe immobilized on a fluorescent bead. Polymerization product is detected by observing the agglutination of the labeled probe and the polymerized polynucleotide product, e.g., visually through a translucent cover disposed over the binding region. Methods and apparatus for mesoscale PCR analyses are described in U.S. application Ser. No. 07/877,662, the disclosure of which is incorporated herein by reference.

Figure 21:
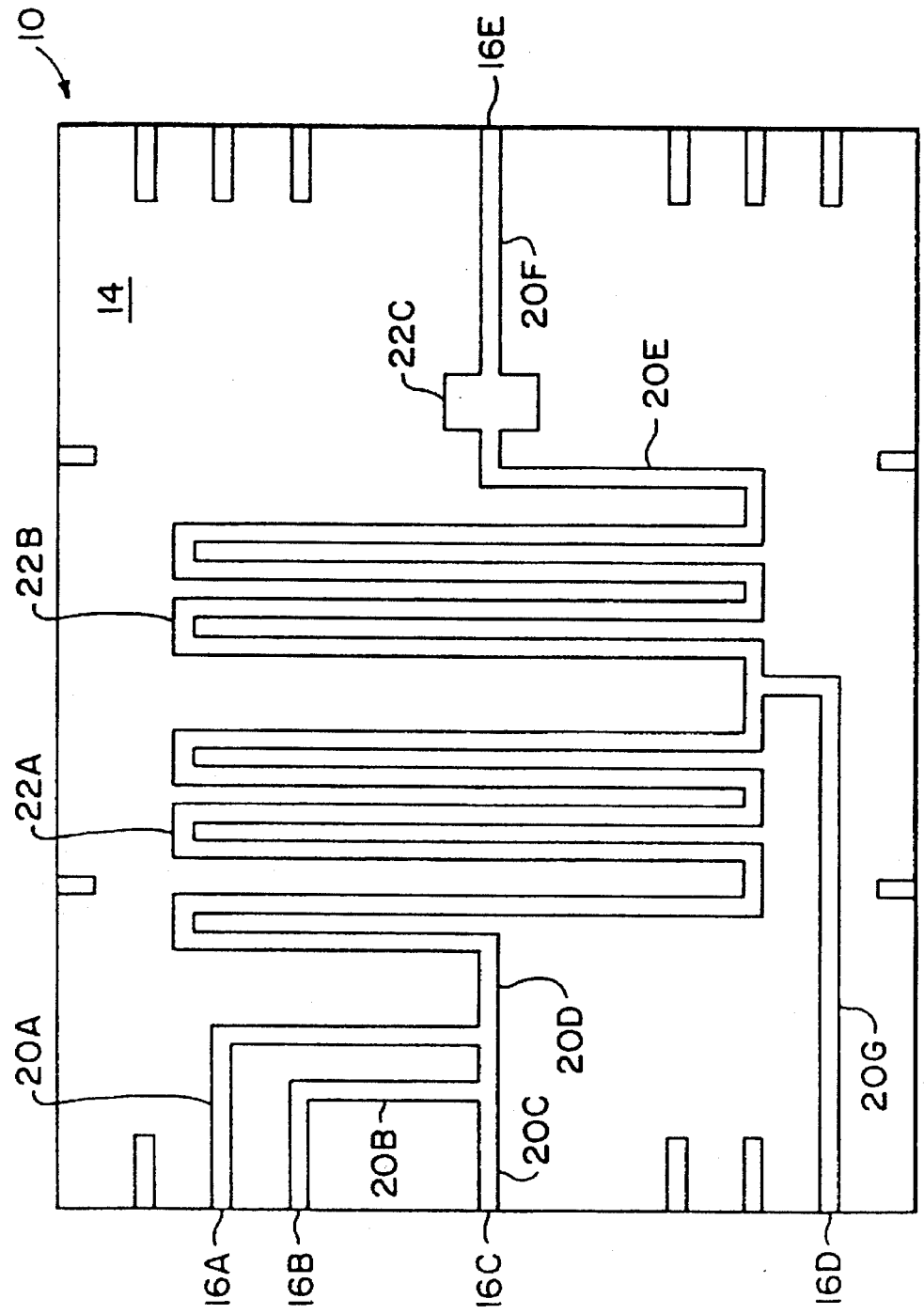
FIG. 21 is a schematic plan view of device 10 microfabricated with a mesoscale flow system that includes the tortuous channels 22A and 22B which allow the timed addition and mixing of assay components during an assay.

In another embodiment, the devices may be utilized to perform an enzyme reaction in which the mixing and addition of sample and reagent components is timed, as is illustrated in the device 10 shown schematically in FIG. 21. The substrate 14 of device 10 is microfabricated with inlet ports 16, flow channels 20, the reaction chambers 22A and 22B and the binding chamber 22C. The reaction chambers 22A and 22B each comprise a tortuous mesoscale flow channel. The path length of the tortuous channel can be designed to permit the timed mixing and addition of sample and reagent components. The device may be utilized in combination with an appliance with ports mated to ports in the device, capable of delivering and receiving fluids through the flow system of the device, and optionally, capable of optically detecting a positive result in the binding chamber. In one embodiment, the cholesterol content of a sample may be assayed. Cholesterol esterase is applied via inlet port 16A, and buffer and sample are added via inlet ports 16B and 16C. The mixture then flows through channel 20D to the tortuous mixing/reaction channel 22A. The time of mixing and reaction may be predetermined by microfabricating the tortuous channel with the appropriate length. Cholesterol oxidase is added via port 16D and flows through channel 20G to the tortuous channel 22B, where the timed mixing and reaction of the oxidase with the fluid from channel 22A occurs. A positive result can be detected optically by observing the binding chamber 22C through an optical window disposed over the substrate. The binding chamber 22C may be provided with a binding moiety capable of detectably reacting with the product of the enzyme reaction. The device may be applied to a range of clinical enzymatic and other reactions.

Optionally, depending on the protocol being exploited in the structure of the chip, the appliance may also be designed to inject reagents necessary to complete the assay, e.g., inject a binding protein tagged with an optically detectable moiety, a substrate solution, or other reagents. The pressure of fluid flow in the mesoscale flow channel 20 in device 10 can be detected by the pressure detectors 54 provided in appliance 50. A microprocessor may be included in the appliance to assist in the collection of data for one or a series of assays. In order to enhance the accuracy of an assay, the substrate may be fabricated to include a control region in the flow system, e.g., a region which does not include binding moieties, such that the sample is directed to both the binding and control regions. Data obtained from sample fluid flowing through the control region may be detected and compared with the data from the sample binding region to increase the precision of the assay.

It will be understood that the above descriptions are made by way of illustration, and that the invention may take other forms within the spirit of the structures and methods described herein. Variations and modifications will occur to those skilled in the art, and all such variations and modifications are considered to be part of the invention, as defined in the claims.

The invention will be understood further from the following nonlimiting examples.

EXAMPLE 1

Figure 6:
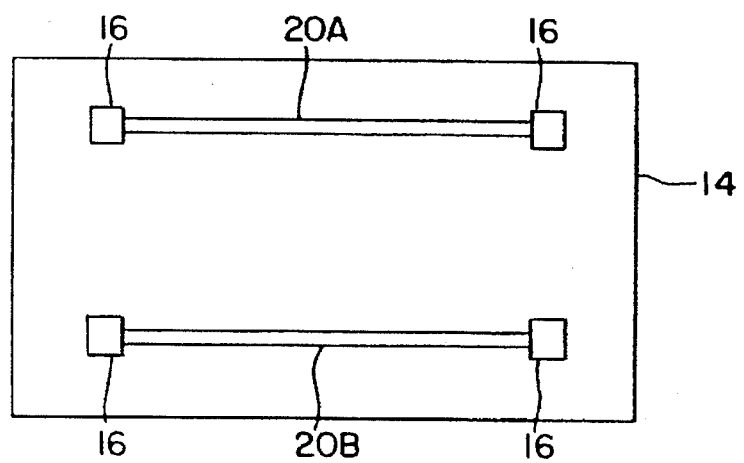
FIG. 6 is a schematic illustration of a top view of a device comprising a substrate 14, microfabricated with a pair of mesoscale flow systems which include inlet ports 16 and flow channel 20.

Capillary agglutination of red blood cells and immobilized anti-A antiserum was examined in a series of silicon substrates 14 (shown schematically in FIG. 6), fabricated with flow channels 20 of varying width. The silicon substrates 1–5 included flow channels 20A and B with a depth of 10 μm and widths ranging from 20 to 300 μm (Table 2). The inside surface of the channels were coated with anti-A (1:10 dilution) by first filling the channel with the antibody (capillary action) and allowing it to dry. A Type blood (diluted 1:5) was then introduced into channel 20 from inlet port 16 by capillary action and the channel was observed visually using a microscope (Leitz Aristomet). Results are summarized in Table 2.

TABLE 2

| SUBSTRATE # | DEPTH (μm) | CHANNEL WIDTH (μm) | AGGLUTINATION |
|---|---|---|---|
| 1 | 10 | A:20 | + |
|   |    | B:40 | + |
| 2 | 10 | A:60 | + |
|   |    | B:80 | + |
| 3 | 10 | A:100 | + |
|   |    | B:120 | + |
| 4 | 10 | A:150 | + |
|   |    | B:200 | + |
| 5 | 10 | A:250 | + |
|   |    | B:300 | + |

EXAMPLE 2

Figure 7:
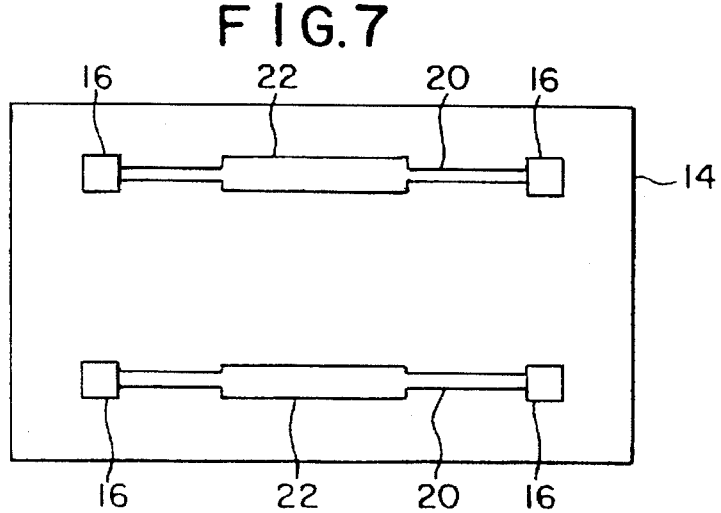
FIG. 7 is a schematic illustration of a top view of another device comprising substrate 14, fabricated with a mesoscale flow system that includes inlet ports 16, flow channel 20 and sample detection chamber 22.

A plastic-silicon hybrid was fabricated by attaching a plastic (3M transparency sheet) cover over the silicon substrate 14, which is microfabricated with flow channels 20 with entry ports 16 on opposite sides of the channel and a central binding chamber 22 (shown schematically in FIG. 7). A dilution of anti-A (in 0.05M sodium bicarbonate pH 9.6) and a 1:10 dilution of Type A blood in saline were introduced via syringe using a holder into the entry ports 16 on opposite ends of the channel 20. The solutions mixed together in the central chamber 22 and agglutination was observed through the plastic cover by light microscopy. The results are summarized in Table 3.

TABLE 3

| ANTI-A | DILUTION | AGGLUTINATION IN CHANNEL |
|---|---|---|
| Gamma Kit | 1:20 | + |
| Gamma Murine Mono | 1:20 | + |
| Gamma Human Dilution | 1:5 | + |
| Immucor Affinity pure | 1:100 | + |
| Immucor Ascites | 1:100 | + |

EXAMPLE 3

A plastic-silicon hybrid was fabricated by attaching a piece of plastic (3M transparency sheet) over a silicon substrate 14 etched with a mesoscale flow channel 20 having entry ports 16 microfabricated on opposite sides of the channel and a central mesoscale mixing chamber 22 (shown schematically in FIG. 7). A solution of mouse IgG (50

μg/mL in 0.05M sodium bicarbonate pH 9.6) (SIGMA Cat. no. 1-5381) and a 1:20 dilution of goat anti-mouse IgG (H&L)—fluorescence carboxylate beads (Polysciences, Inc.) in PBS buffer were introduced via syringe using a holder into the entry ports on opposite ends of the channel. The solutions mixed together in the central chamber 22 and agglutination was observed through the transparent plastic cover by light microscopy.

EXAMPLE 4

Figure 8:
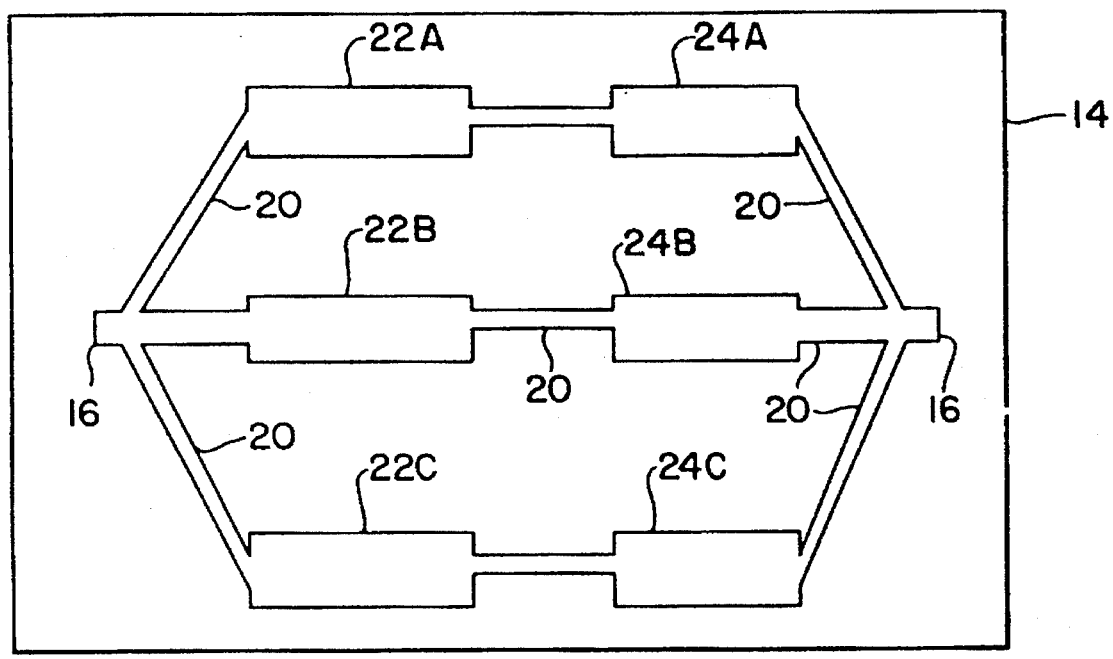
FIG. 8 is a schematic illustration of a top view of a solid substrate 14 microfabricated with three flow paths 20 each of which defines a pair of detection chambers 22 and 24. Chambers 22A, 22B and 22C contain antibodies to group A blood antigen, group B blood antigen and Rhesus antigen respectively, while chambers 24A, 24B and 24C are control chambers.

An analytical element 14 having three pairs of mesoscale analytical chambers 22A–C, linked to three pairs of mesoscale control chambers 24A–C emanating from entry port 16 is used for the determination of the blood group of a blood sample (shown schematically in FIG. 8). The surface of chamber 22A is sensitized with antibody to blood group A antigen, chamber 22B is sensitized with antibody to blood group B antigen and chamber 22C is sensitized with antibody to Rhesus antigen. The surface of chambers 24A, 24B and 24C are untreated and used as negative controls. A finger prick sample of blood is drawn into the device through port 16 using a syringe. Binding of red cells to the surface of the three chambers 22A–C is observed. The presence of red cells on the surface of a particular chamber (22A, 22B and/or 22C) denotes a positive result for the blood group antigen. The analytical device containing the sample is then discarded.

EXAMPLE 5

Figure 9:
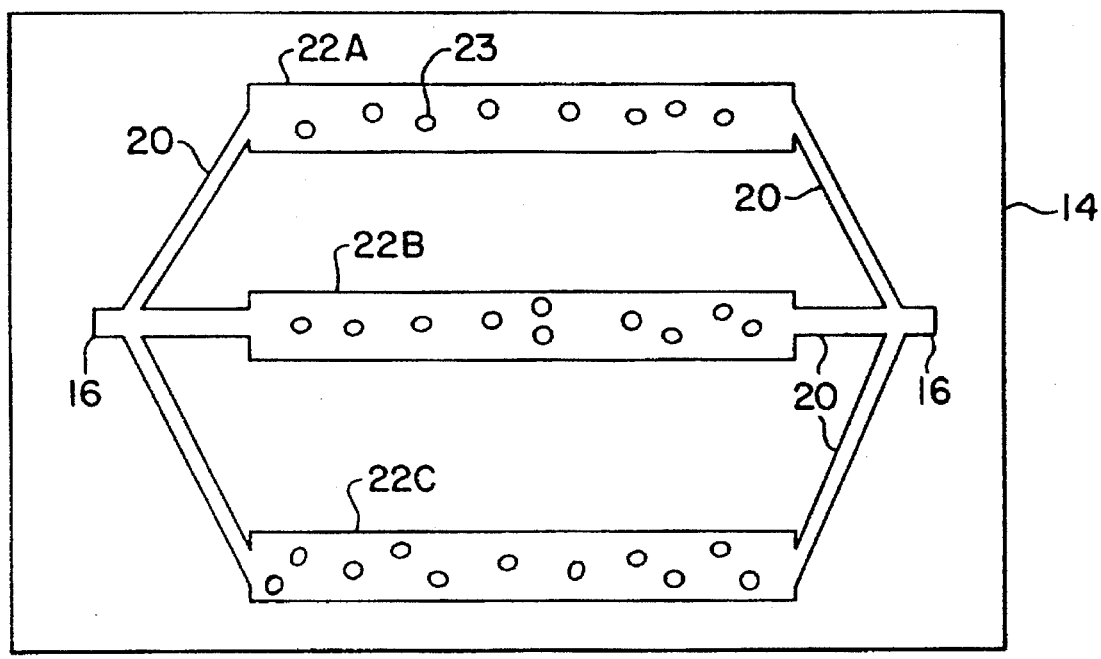
FIG. 9 is a schematic illustration of a top view of a solid substrate 14 microfabricated with three sample detection chambers 22A, 22B and 22C containing beads on which are immobilized antibodies to group A blood antigen, group B blood antigen and Rhesus antigen respectively.

An analytical element 14 (shown schematically in FIG. 9) having three chambers, 22A, 22B and 22C, linked by channels 20 emanating from inlet port 16 is used for the determination of the blood group of a blood sample. Chamber 22A contains beads sensitized with antibody to blood group A antigen, chamber 22B contains beads sensitized with antibody to blood group B antigen, and chamber 22C contains beads sensitized with antibody to Rhesus antigen. A finger prick sample of blood is drawn into the device using a syringe. Binding of red cells to the beads and subsequent agglutination in the chambers is observed. The presence of agglutinated red cells in a particular chamber denotes a positive result for the blood group antigen. The analytical device containing the sample is then discarded.

EXAMPLE 6

An analytical element 14 (shown schematically in FIG. 8) having three pairs of chambers 22A, 22B and 22C linked by channels 20 emanating from entry ports 16 is used for the determination of the blood group of a blood sample. The element also includes the control chambers 24A, 24B and 24C. The surface of chamber 22A is sensitized with antibody to blood group A antigen, chamber 22B is sensitized with antibody to blood group B antigen, and chamber 22C is sensitized with antibody to Rhesus antigen. The surface of chambers 24A–C are untreated and act as negative controls. A finger prick sample of blood is mixed with a fluorescent dye and then drawn into the inlet port 16 using a syringe. Binding of the fluorescent red cells to the surface in the three chambers (22A, 22B, and/or 22C) is rapidly observed using a microfluorometer and denotes a positive result for the blood group antigen. The analytical device containing the sample is then discarded.

EXAMPLE 7

The growth of an organism is monitored in the device shown schematically in FIG. 4. The fractal pattern of mesoscale flow paths 40 in the substrate 14 are filled via inlet port 16A with 2 μL of a mixture of growth medium which has been inoculated with a sample of a test specimen. The device is sealed and incubated for 60 minutes at 37° C. Growth is detected by visual inspection using a microscope or by determining the flow properties of the channel system, e.g., via the electrical conductivity probe 17. The absence of flow indicates growth and consequent blockage of the channel system.

EXAMPLE 8

Figure 14:
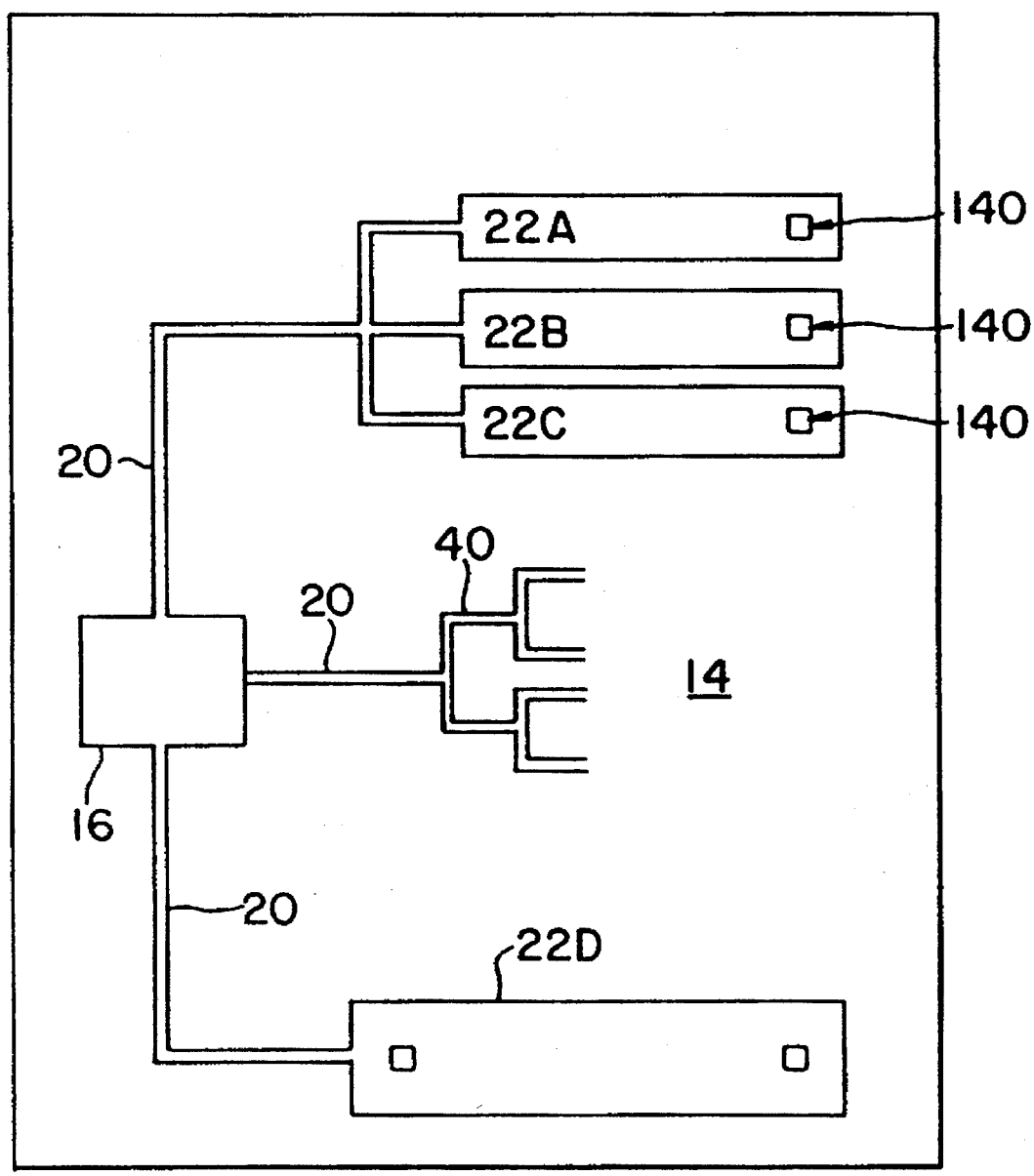
FIG. 14 is a schematic plan view of a sperm function testing apparatus constructed in accordance with the invention.

Sperm functions are tested on the microfabricated solid substrate 14 shown in FIG. 14. A sperm sample is added to the inlet port 16 and then flows through the mesoscale flow channel 20 to the binding chambers 22A–D each having a reagent addition port 140. Detection chamber 22A provides a test for leucocytes and includes beads containing immobilized antibody to common leukocyte antigen. Detection chamber 22B provides a test for sperm antibodies and contains beads on which are immobilized antibody to human IgG (e.g., Bio-Rad, Immunobead Cat. No. 170–5100). Chamber 22C provides a test for acrosome reaction and contains fluorescein labeled lectin. Chamber 22D provides a test for sperm-cervical interaction and contains hyaluronic acid or bovine cervical mucus. Agglutination in the chambers may be detected either optically manually or by machine. The fractal pattern of flow channels 40 is used to test flow properties of the sample. The distance that the sperm sample travels along the fractal flow path serves as an indicator of sperm motility. Alternatively, mesoscale flow systems fabricated with other configurations may be utilized, such as a nonbranching flow channel.

EXAMPLE 9

A polymerase chain reaction is performed in the device illustrated schematically in FIG. 15, to detect the presence of a polynucleotide in a fluid sample. The device 10 shown in FIG. 15 includes a solid substrate 14 microfabricated with inlet ports 16A–D connected to the mesoscale flow channel 20. Mesoscale flow channel 20 also is provided with PCR reaction chambers 164 and 166, filters 168 and binding chamber 22. The device 10 is used in combination with an appliance, such as appliance 50 in FIG. 5, that is provided with fluid channels, a fluid pump and temperature control elements for controlling the temperature of reaction chambers 164 and 166. The appliance also includes fluid flow paths with valves in fluid communication with ports 16A, 16B, 16C, and 16D allowing the ports to be reversibly opened or closed during an assay.

To perform a PCR analysis to detect a polynucleotide in a cell, a sample cell lysate is added to a buffered solution of Taq polymerase, nucleoside triphosphates, polynucleotide primers and other reagents required for a PCR assay. The cell sample lysate is delivered via the appliance through entry port 16A to PCR reaction chambers 164 and 166. Ports 16A and 16D are closed by means of valves included in the appliance, while port 16B and 16C are open. Means such as electrical means are included in the appliance to regulate the temperature of the reaction chambers 164 and 166. A pump in the appliance connected through port 16B is used to cycle sample fluids between reaction chamber 164, set at 94° C., for polynucleotide dehybridization, and reaction chamber 166, set at 65° C., for polymerase reaction. Port 16C serves as a vent. After the polymerase chain reaction is complete, port 16C is closed and 16D is opened and the pump in the appliance connected to port 16B is used to deliver the sample from the PCR reaction chambers 164 and 166 to the binding chamber 22. Detection chamber 22 is provided with fluorescent labeled beads on which are immobilized polynucleotide probes capable of binding the amplified polynucleotide. The agglutination of the amplified polynucleotide with the labeled polynucleotide probe is detectable through a window disposed over the binding region 22 and provides a test for the presence of amplified polynucleotide product.

EXAMPLE 10

Figure 16:
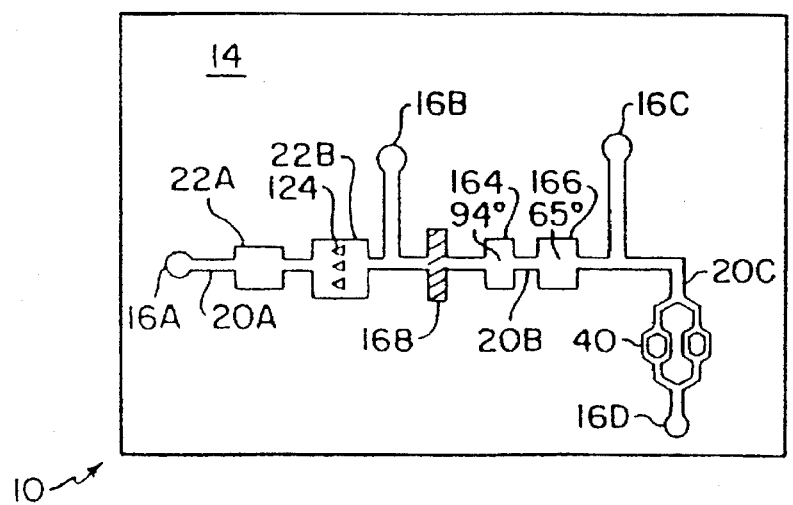
FIG. 16 is a schematic top view of a analytical device fabricated with a series of mesoscale chambers suitable for implementing a variety of functions including cell sorting, cell lysing and PCR analysis.

A multitest device 10 including substrate 14, shown schematically in FIG. 16, is used to detect the presence of an intracellular polynucleotide in a biological cell-containing fluid sample. The device is used in combination with an appliance, such as appliance 50, shown in FIG. 5. The appliance includes fluid channels with ports, that include valves that may be reversibly opened and closed, mated to the ports in device 10, allowing the ports in the device to be mechanically opened and closed during an assay. The appliance also includes means, such as electrical contacts mated to contacts imbedded in the substrate 14, for regulating the temperature of reaction chambers 164 and 166. The appliance further includes a pump to control the flow of fluid through the device 10.

Initially, the valves in the appliance are used to close ports 16C and 16D, while ports 16A and 16B remain open. The sample is directed to the sample inlet port 16A by a pump in the appliance, and flows through the mesoscale flow path 20A to chamber 22A, which contains binding moieties immobilized on the wall of the chambers for selectively binding to a surface molecule on a desired cell population. After binding of the desired cell population in chamber 22A, flow with buffer is continued, exiting through port 16B, to purify and isolate the cell population. Port 16B is then closed and port 16C is opened. Flow is then increased sufficiently to dislodge the isolated cells from the surface of chamber 22A to chamber 22B where membrane piercing protrusions 124 in chamber 22B tear open the cells releasing intracellular material.

Sample flow continues past filter 168, which filters off large cellular membranes and other debris, to the mesoscale PCR chambers 164 and 166. The valves in the appliance are used to open port 16B and to close port 16A. Taq polymerase, primers and other reagents required for the PCR assay are added to chambers 164 and 166 through port 16C from a mated port and flow path in the appliance. A pump in the appliance connected via port 16B is used to cycle the PCR sample and reagents between chambers 164 and 168, set at 94° C. and 65° C. respectively, to implement a polynucleotide dehybridization and polymerization cycle, allowing the production and isolation of product polynucleotide. The valves in the appliance are used to close port 16C and to open port 16D. The pump in the appliance connected to port 16B is used to direct the polymerized polynucleotide isolated from the cell population to the fractal binding region 40, which contains immobilizing binding moieties, such as a complementary polynucleotide probe. Flow restriction in the fractal region 40 indicates a positive assay for the intracellular polynucleotide.

EXAMPLE 11

A chemiluminescent peroxyoxylate organic phase reaction was conducted in a mesoscale flow channel. A Cyalume™ light stick (Aldrich, Milwaukee, Wis.) was opened and the mixture of peroxyoxylate and fluorophore (component A) were drained into a test tube. The glass vial containing the oxidant was removed and washed with alcohol. The contents of the vial (component B) were transferred to a test tube. A 100 μL sample of component A and 50 μL of component B were mixed together to initiate the chemiluminescent reaction.

A sample of the fluorescent solution was introduced into the central inlet port of chip #6, provided with a chamber with dimensions of 812 μm in width, 400 μm in depth and 5.2 mm in length, connected to two 20 μm deep, 100 μm wide, 3.25 mm long channels. Any excess sample was wiped off the surface of the chip, and the chip was placed into a modified microwell strip holder. The light emission from the mesoscale flow channel was measured using an Amerlite microplate reader (Amersham Diagnostics Ltd., Amersham, UK). A similar experiment was performed using a 300 μm wide, 20 μm deep mesoscale flow channel (volume 70.2 pL) in chip #5. Light emission (peroxyoxylate chemiluminescence) was detected and measured in units of RLU (relative light units) from the mesoscale flow channels in the different chips using the luminescence microplate reader (Table 4).

TABLE 4

| Chip | Channel Volume | Light Emission (RLU) |
|---|---|---|
| #6 | 1702 pL | 718.26 |
| #5 | 70.2 pL | 35.63 |

EXAMPLE 12

In an aqueous phase reaction, the chemiluminescent horseradish peroxidase catalyzed oxidation of isoluminol was examined. The luminol-hydrogen peroxide reagent was prepared as follows: Sodium luminol (12.5 mg) was dissolved in 50 mL of Tris buffer (0.1 mol/L, pH 8.6). 15.5 pL of hydrogen peroxide (30% w/v) was mixed with 0.5 mL of Tris buffer (0.1 mol/L, pH 8.6). These two solutions were combined and protected from light. The luminol-hydrogen peroxide reagent (100 μL), 5 μL of 4-iodophenol ((Aldrich) (1 mg/ml in 0.1 mol/L Tris buffer, pH 8.6), and 10 μL of a dilution of horseradish peroxidase (Type VIA, 1 mg/mL) in Tris buffer (0.1 mol/L, pH 8.6) were mixed together. A sample of this solution was introduced into the central chamber of chip #6 or into the 300 μm channel of chip #5. The light emission was then measured using the Amerlite microplate reader.

The chemiluminescence emission from the horseradish peroxidase catalyzed oxidation of luminol in the different mesoscale channels was detected using the luminescence microplate reader. A peroxidase assay using dilutions of the stock peroxidase gave a dose dependent relationship (Table 5).

TABLE 5

| Chip | Channel Volume | Peroxidase dilution | Light Emission (RLU) |
|---|---|---|---|
| #6 | 1702 pL | undiluted | 0.18* |
|  |  | 1:10 | 4.68 |
|  |  | 1:100 | 2.23 |
|  |  | 1:1000 | 1.82 |
| #5 | 70.2 pL | undiluted | 2.09 |

*Low light level because of substrate exhaustion.

EXAMPLE 13

Chemiluminescent reactions in the mesoscale flow channels were detected photographically. Mesoscale channels of chip #6 were filled with the peroxyoxylate or horseradish peroxidase (10 µg/mL)- luminol-peroxide reaction mixtures as described in Example 11 and 12. The light emission was detected by contacting the chip with instant photographic film (Polaroid, Type 612) in a camera luminometer (Wolfson applied Technology, Birmingham, UK). Light emission from the different chemiluminescent reactions in the mesoscale flow channels was detected using high speed instant photographic film (Table 6). The lower light intensity from the peroxidase reaction required a longer exposure time.

TABLE 6

|  | Exposure Time | Detected (D) Not Detected (ND) |
| --- | --- | --- |
| Peroxyoxylate reaction | 1 second | D |
| | 5 minutes* | D |
| Horseradish peroxidase reaction | 10 minutes | D |

*After 2 day incubation at room temperature.

EXAMPLE 14

An experiment testing different spermicides using a mesoscale flow system was conducted. A chip comprising two chambers (5.2 mm long, 750 µm wide, 1.5 mm deep) each linked at each end to an entry hole by a channel (3.25 mm long, 100 µm wide, 20 µm deep) was used for the simultaneous testing of the spermicidal activity of nonoxynol-9 and C13-G (Biosyn, Inc., Pa.). The four channels were filled with HTF-BSA solution (channel #1, control), 0.005% (channel #2), 0.0125% (channel #3), and 0.05% (channel #4) nonoxynol-9 (or C13-G), respectively. A sample of semen was placed in each chamber, and the progress of sperm into the adjoining channels monitored using the microscope. The number of sperm observed in the channels was in the following order of decreasing sperm count: channel #1>#2>#3>#4. The most sperm were seen in the control channel, and none were seen in channel #4 which contained nonoxynol-9 or C13-G at the optimum concentration for spermicidal action.

EXAMPLE 15

The interaction of a sperm sample with cervical mucus in a mesoscale flow system was tested in a chip comprising two chambers (5.2 mm long, 750 µm wide, 1.5 mm deep) each linked at each end to an entry hole by a channel (3.25 mm long, 100 µm wide, 20 µm deep). The channels were filled with HTF-BSA solution and a cervical mucus sample (collected at approximately day 14 of the patient's menstrual cycle) placed in each of the central chambers. Sperm did not migrate into the cervical mucus and those that penetrated died, as anticipated because cervical mucus is known to be hostile to sperm at this time during the menstrual cycle. Moghissi et al., *Am. J. Obstet. Gynecol.*, 114:405 (1972).

EXAMPLE 16

A test of the interaction of hyaluronic acid with a sperm sample was conducted to assess the cervical interaction properties of a sperm sample. The test was conducted in a chip comprising two chambers (5.2 mm long, 750 µm wide, 1.5 mm deep) each linked at each end to an entry hole by mesoscale flow Channels #1, #2, #3 and #4 (3.25 mm long, 100 µm wide, 20 µm deep). Channel #1 was a control channel. Channels were filled with HTF-BSA solution and solutions of hyaluronic acid (Sigma) in HTF-BSA (channels #2, #3, #4, 5 mg/mL, 2.5 mg/mL, and 1.3 mg/mL, respectively). A semen sample was placed in each of the central chambers. Sperm did not migrate into channel #2, containing 5 mg/mL hyaluronic acid, but the extent of migration increased as the concentration of hyaluronic acid decreased in channels #3 and #4.

EXAMPLE 17

An immunobead test for the presence of IgG antibodies in a sperm sample was conducted. Immunobeads (BioRAD, Richmond, Calif.), microbeads coated with an antibody to human IgG, were diluted to 1 mg/mL in HTF-BSA solution (Irvine *Scientific, Santa Ana, Calif.*). A microchannel (250 µm wide, 20 µm deep, and 10 mm long) in a glass-silicon chip was filled with a sample of the immunobead solution and a semen sample (ca 1.2 µL) was applied to the channel entry. Agglutination of sperm by the immunobeads due to the presence of antibodies in the sperm sample was observed in the channel. As a control, the experiment was performed on a glass microscope slide using larger volumes of the immunobead reagent and semen sample, and this was also positive (agglutination observed).

It will be understood that the above descriptions are made by way of illustration, and that the invention may take other forms within the spirit of the structures and methods described herein. Variations and modifications will occur to those skilled in the art, and all such variations and modifications are considered to be part of the invention, as defined in the claims.

What is claimed is:

1. A device for detecting the presence of an analyte in a fluid sample, the device comprising:
   a solid substrate microfabricated to define:
      a sample inlet port, said port being dimensioned for connection to a pump means; and
      a mesoscale flow system comprising:
         a sample flow channel extending from said inlet port; and
         an analyte binding region in fluid communication with said flow channel comprising a binding moiety immobilized on a surface in said analyte binding region, wherein said binding moiety specifically binds to analyte in said fluid sample, at least one of said sample flow channel or said analyte binding region having mesoscale cross-sectional dimensions; and
      a binding means associated with said analyte binding region or in fluid communication with said analyte binding region for detecting binding of said analyte to said binding moiety.

2. The device of claim 1, wherein said binding moiety is immobilized on a surface of a solid particle in said binding region.

3. The device of claim 1, wherein said analyte and said immobilized binding moiety comprise a ligand/receptor pair.

4. The device of claim 1, wherein said analyte is an intracellular molecular component in a cell-containing liquid biological sample, said device further comprising:
   cell lysing means in said mesoscale flow system in fluid communication with said flow channel, said analyte binding region being downstream from said cell lysing means; and
   means for engaging cells in said cell-containing sample with said cell lysing means, thereby to release said intracellular molecular component.

5. The device of claim 4, wherein said cell lysing means comprises a portion of said flow channel having cell-membrane piercing protrusions extending from a wall thereof.

6. The device of claim 4, wherein said cell lysing means comprises a region of restricted cross-sectional dimension sufficient to permit passage of intracellular molecules while prohibiting passage of cells.

7. The device of claim 4, wherein said analyte is a cell population in said sample, said device further comprising:
   a cell separation region, upstream from said analyte binding region comprising an immobilized cell binding moiety that binds cell surface molecules of said cell population; and
   pump means for inducing flow of said sample to said separation region.

8. The device of claim 1, wherein said solid substrate comprises microfabricated silicon.

9. The device of claim 1, wherein said sample flow channel and said binding region are microfabricated in a surface of said solid substrate and enclosed by a cover adhered to said surface.

10. The device of claim 1, wherein said binding means comprises a window for optically probing said analyte binding region, said window being disposed over said analyte binding region on said substrate.

11. The device of claim 10, wherein said analyte binding region comprises particles having said analyte specific binding moiety immobilized on the surface thereof which, in the presence of an analyte, induce particle agglomeration optically detectable through said window.

12. The device of claim 10, wherein said substrate further defines a control region in fluid communication with said sample inlet port and a control region window, disposed over said control region on said substrate, for optically probing said control region whereby data determined optically in said control and analyte binding regions may be compared.

13. The device of claim 10, wherein said flow system further comprises:
   a fractal region in fluid communication with said flow channel comprising bifurcations leading to plural secondary flow channels; and
   pump means for inducing flow of a biological sample through said flow channel and said fractal region.

14. The device of claim 1, wherein the width and depth of said flow channel each are between 2.0 um and 500 um.

15. A device for detecting the presence of an analyte in a fluid sample, the device comprising:
   a solid substrate microfabricated to define:
      a sample inlet port; and
      a mesoscale flow system comprising:
         a sample flow channel extending from said inlet port; and
         an analyte binding region in fluid communication with said flow channel comprising a binding moiety immobilized on a surface of said analyte binding region, wherein said binding moiety specifically binds to analyte in said sample, at least one of said sample flow channel or said analyte binding region having mesoscale cross-sectional dimensions;
      a pump means for delivering to said analyte binding region a labelled substance which binds analyte bound to said binding moiety to produce an optically detectable signal indicative of the presence of said analyte; and
   a binding means associated with said analyte binding region or in fluid communication with said analyte binding region for detecting said optically detectable signal, thereby to determine the presence of the analyte.

16. The device of claim 15, wherein said binding means comprises:
   a window for optically probing said analyte binding region, said window being disposed over said analyte binding region on said substrate; and
   optical binding means disposed over said window for detecting the presence of said detectable signal through said window.

17. The device of claim 15, wherein said optically detectable signal is a luminescent signal.

18. The device of claim 15, wherein said optically detectable signal is a fluorescent signal.

19. A device for detecting the presence of multiple analytes in a fluid sample, the device comprising:
   a solid substrate microfabricated to define:
      a sample inlet port; and
      a first and at least a second mesoscale flow system, each said flow system comprising:
         a sample flow channel extending from said inlet port; and
         an analyte binding region in fluid communication with said flow channel comprising binding moiety immobilized on a surface in said analyte binding region, wherein said binding moiety specifically binds to analyte, at least one of said sample flow channel or said analyte binding region having mesoscale cross-sectional dimensions; and
   a binding means associated with each analyte binding region or in fluid communication with each analyte binding region for detecting the binding of analyte to the binding moiety in each analyte binding region, thereby to determine the presence of said analyte; and
   wherein the analyte binding regions of said flow systems comprise different immobilized binding moieties capable of binding different analytes.

20. A device for detecting the presence of an analyte in a fluid sample, the device comprising:
   a solid substrate microfabricated to define:
      a sample inlet port; and
      a mesoscale flow system comprising:
         a tortuous sample flow channel extending from said inlet port, wherein said tortuous flow channel is microfabricated with a length which allows timed mixing of reagents and sample fluid; and
         an analyte binding region in fluid communication with said tortuous flow channel comprising a binding moiety immobilized on a surface in said analyte binding region, said binding moiety specifically binds to said analyte, at least one of said sample flow channel or said analyte binding region having mesoscale cross-sectional dimensions; and
      a binding means associated with said analyte binding region or in fluid communication with said analyte binding region for detecting the binding of analyte to the binding moiety thereby to determine the presence of the analyte.

21. A method for detecting the presence of an analyte in a fluid sample, the method comprising the steps of:
   (i) providing a device comprising:
      a solid substrate microfabricated to define:
         a sample inlet port, said port being dimensioned for connection to a pump means; and
         a mesoscale flow system comprising:
            a sample flow channel extending from said inlet port; and an analyte binding region in fluid communication with said flow channel comprising a binding moiety immobilized on a surface in said analyte binding region, wherein said binding moiety specifically binds to said analyte, at least one of said sample flow channel or said analyte binding region having mesoscale cross-sectional dimensions; and a binding means associated with said analyte binding region or in fluid communication with said analyte binding region for detecting binding of said analyte to said binding moiety, thereby to determine the presence of said analyte;

(ii) delivering a sample to said inlet port and, by a pump means, through said flow system to said analyte binding region to permit binding of said analyte to said binding moiety; and (iii) detecting the binding of analyte to said binding moiety with said binding means, thereby to determine the presence of the analyte.

22. The method of claim 21, wherein said binding means in the device provided in step (i) comprises a window disposed over said analyte binding region on said substrate; and wherein step (iii) includes the step of optically probing said binding region through said window.

23. The method of claim 22, wherein said substrate provided in step (i) further defines a control region in fluid communication with said sample inlet port and a control region window, disposed over said control region on said substrate, for optically probing said control region whereby data determined optically in said control and analyte binding regions may be compared; and wherein step (iii) includes the step of optically probing and comparing said control region and said binding region.

24. The method of claim 21, wherein the device provided in step (i) further includes:

a pump means for delivering to said analyte binding region a labelled substance which binds to analyte bound to said binding moiety to produce a detectable signal indicative of the presence of said analyte; and means for detecting the binding of the labelled substance to analyte bound to said binding moiety;

said method further comprising the steps of:

(iv) delivering said labelled substance to said analyte binding region to bind to said bound analyte; and (v) detecting said detectable signal with said binding means, thereby to determine the presence of the analyte.

25. The method of claim 24, wherein said detectable signal comprises a luminescent signal.

26. The method of claim 21, wherein said sample comprises a cell population, said method comprising the additional step of separating said cell population from other cells within said substrate prior to step (iii).

27. The method of claim 21, wherein the width and depth of said flow channel each are between 2.0 um and 500 um.

28. The method for detecting the presence of a cell population in a sample, the method comprising the steps of:

(i) providing a device comprising:

a sample inlet port, said port being dimensioned for connection to a pump means; and a mesoscale flow system comprising:

a sample flow channel extending from said inlet port; and an analyte binding region in fluid communication with said flow channel comprising a binding moiety immobilized on a surface in said analyte binding region, wherein said binding moiety specifically binds a surface molecule on members of said cell population, at least one of said sample flow channel or said analyte binding region having mesoscale cross-sectional dimensions; and a window disposed over said analyte binding region on said substrate;

(ii) delivering a sample to said inlet port and, by a pump means, through said flow system to said binding region, to permit said binding moiety to bind to a surface molecule on members of said cell population to induce agglutination of said cell population on the surface of said binding region; and (iii) detecting said agglutination optically in said binding region through said window, thereby to determine the presence of the cell population in the sample.

29. A method for detecting the presence of one or more analytes in a fluid sample, the method comprising the steps of:

(i) providing a device comprising:

a solid substrate microfabricated to define:

a sample inlet port; and a first and at least a second mesoscale flow system, each said flow system comprising:

a sample flow channel extending from said inlet port; and an analyte binding region in fluid communication with said flow channel comprising binding moiety immobilized on a surface in said analyte binding region, wherein said binding moiety specifically binds to analyte, at least one of said sample flow channel or said analyte binding region having mesoscale cross-sectional dimensions; and a detection means associated with each analyte binding region or in fluid communication with each analyte binding region for detecting binding of analyte to the binding moiety in each analyte binding region, thereby to determine the presence of said analyte;

(ii) delivering a sample to said inlet port and, by pump means, through said flow system to a said analyte binding regions; and (iii) detecting the binding of an analyte to the binding moiety in each of the analyte binding regions in said first and at least second system with said binding means, thereby to determine the presence of the analytes.

30. In combination, a device for determining an analyte in a fluid sample, said device comprising a solid substrate having at least one surface and being microfabricated to define:

a sample inlet port; and a flow system comprising:

a sample flow channel extending from said inlet port; and an analyte binding region in fluid communication with said flow channel comprising a binding moiety which specifically binds to said analyte, at least one of said sample flow channel or said analyte binding region having mesoscale cross-sectional dimensions;

detection means associated with said analyte binding region or in fluid communication with said analyte binding region for detecting binding of said analyte to said binding moiety; and an appliance for use with said device, said appliance comprising a holder for said device, a fluid sample input conduit interfitting with said inlet port of said device and a pump for passing fluid sample through said flow system.

31. The combination of claim 30, wherein the analyte binding region of said device has mesoscale cross-sectional dimensions.

32. The combination of claim 30, wherein the flow channel of said device has mesoscale cross-sectional dimensions.

33. The combination of claim 30, wherein said binding moiety is immobilized on a surface within the analyte binding region of said device.

34. The combination of claim 30, wherein said appliance further comprises a fluid reservoir and means for delivering fluid contained in said reservoir to said flow system.

35. The combination as claimed in claim 34, wherein said reservoir contains a labelled reagent which produces a detectable signal when bound to said analyte.

36. The combination of claim 30, wherein said analyte binding region comprises particles having analyte binding moieties immobilized on the surface thereof which in the presence of said analyte, induce particle agglomeration.

37. The combination of claim 30, wherein the flow system of said device is microfabricated in a surface of said solid substrate and enclosed by a transparent cover adhered to said surface.

38. The combination of claim 30, wherein said analyte is a ligand and said binding moiety is a receptor which binds specifically to said ligand.

39. The combination of claim 30, wherein said analyte is an antigen and said binding moiety is an antigen binding protein which binds specifically to said antigen.

40. The combination of claim 30, wherein said analyte is a polynucleotide and said binding moiety is a complementary polynucleotide that hybridizes to said polynucleotide analyte.

41. A method for determining the presence or amount of an intercellular component in a cell-containing biological fluid sample, said method comprising the steps of:

(i) providing a device comprising a solid substrate microfabricated to define:
  a sample inlet port; and
  a flow system comprising:
    a sample flow channel extending from said inlet port; and
    an analyte binding region in fluid communication with said flow channel comprising a binding moiety which specifically binds said analyte, at least one of said sample flow channel or said analyte binding region having mesoscale cross-sectional dimensions;
    cell lysing means in said mesoscale flow system, and upstream of said analyte binding region, in fluid communication with said flow channel;
    binding means associated with said analyte binding region or in fluid communication with said analyte binding region for detecting binding of said analyte to said binding moiety;

(ii) delivering said sample to said inlet port;

(iii) lysing said cells within said device to release said intercellular component;

(iv) delivering said intercellular component to said analyte binding region; and (v) detecting binding of said intercellular component to said binding moiety as determinative of the presence or amount of said intercellular component in said sample.

42. The method of claim 41, wherein said intercellular component is in a subpopulation of cells within a mixed cell population in said sample, and said method includes the additional step of separating said cell subpopulation from said mixed cell population within said device prior to said lysing step.

43. The method of claim 41, wherein the device provided in step (i) further includes means for delivering to said bound analyte binding region a labelled reagent which binds to said bound intercellular component to produce a detectable signal indicative of the binding of said intercellular component to said binding moiety, said method further comprising delivering said labelled reagent to said analyte binding region, and, in said detecting step, detecting said signal.

44. The method of claim 41, wherein the analyte binding region in said device provided in step (i) comprises particles having analyte binding sites immobilized on the surface thereof which, in the presence of said intercellular component, induce particle agglomeration, and, as a result of step (iv), said intercellular component binds to said particles to induce agglomeration; and, in said detecting step, detecting said agglomeration.

* * * * *

UNITED STATES PATENT AND TRADEMARK OFFICE
CERTIFICATE OF CORRECTION

PATENT NO. : 5,637,469
DATED : June 10, 1997
INVENTOR(S) : Peter Wilding and Larry J. Kricka and Jay N. Zemel It is certified that error appears in the above-identified patent and that said Letters Patent is hereby corrected as shown below:

Column 22, line 45, change "binding" (first occurrence) to -- detection --;

Column 22, line 50, change "binding" to -- detection --;

Column 23, lines 16, 19 and 23, change "binding" to -- detection --;

Column 23, line 64, change "binding" (first occurrence) to -- detection --;

Column 24, lines 1 and 6, change "binding" to -- detection --;

Column 24, lines 28 and 54, change "binding" (first occurrence in each line) to -- detection --;

Column 25, line 9, change "binding (first occurrence) to -- detection --;

Column 25, lines 19, 21, 26, 35 and 49, change "binding" to -- detection --;

Column 26, lines 12, 16, 17 and 48, change "binding" to -- detection --;

Column 27, line 22, change "binding" (first occurrence) to -- detection --;

Column 28, line 10, change "binding" (first occurrence to -- detection --.

Signed and Sealed this

FourthDay of August, 1998

*Attest:*

BRUCE LEHMAN

*Attesting Officer*     Commissioner of Patents and Trademarks